(12) United States Patent
Wolkenberg et al.

(10) Patent No.: US 9,309,199 B2
(45) Date of Patent: Apr. 12, 2016

(54) INHIBITORS OF CATECHOL O-METHYL TRANSFERASE AND THEIR USE IN THE TREATMENT OF PSYCHOTIC DISORDERS

(75) Inventors: Scott Wolkenberg, Jenkintown, PA (US); James C. Barrow, Harleysville, PA (US); Scott T. Harrison, Glenside, PA (US); B. Wesley Trotter, Newton Highlands, MA (US); Kausik K. Nanda, Norristown, PA (US); Peter J. Manley, Harleysville, PA (US); Zhijian Zhao, Wilmington, DE (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/582,555

(22) PCT Filed: Feb. 28, 2011

(86) PCT No.: PCT/US2011/026414
§ 371 (c)(1),
(2), (4) Date: Sep. 5, 2012

(87) PCT Pub. No.: WO2011/109261
PCT Pub. Date: Sep. 9, 2011

(65) Prior Publication Data
US 2013/0005744 A1 Jan. 3, 2013

Related U.S. Application Data

(60) Provisional application No. 61/310,400, filed on Mar. 4, 2010.

(51) Int. Cl.
| | | |
|---|---|---|
| *C07D 211/86* | (2006.01) | |
| *C07D 213/69* | (2006.01) | |
| *C07D 213/84* | (2006.01) | |
| *C07D 213/85* | (2006.01) | |
| *C07D 401/04* | (2006.01) | |
| *C07D 413/10* | (2006.01) | |
| *C07D 417/04* | (2006.01) | |

(52) U.S. Cl.
CPC ............ *C07D 213/69* (2013.01); *C07D 211/86* (2013.01); *C07D 213/84* (2013.01); *C07D 213/85* (2013.01); *C07D 401/04* (2013.01); *C07D 413/10* (2013.01); *C07D 417/04* (2013.01)

(58) Field of Classification Search
CPC .. C07D 213/69; C07D 213/84; C07D 213/85; C07D 401/04; C07D 413/10; C07D 417/04; C07D 211/86
USPC .......................................... 514/348; 546/296
See application file for complete search history.

(56) References Cited

U.S. PATENT DOCUMENTS

| | | | | |
|---|---|---|---|---|
| 4,225,601 A | * | 9/1980 | Lesher et al. ................ | 514/334 |
| 4,361,569 A | | 11/1982 | Lesher et al. | |
| 4,539,321 A | * | 9/1985 | Campbell ................ | 514/252.03 |
| 4,840,958 A | * | 6/1989 | Hider et al. ................... | 514/348 |
| 6,930,117 B2 | | 8/2005 | Warshakoon et al. | |
| 7,435,734 B2 | | 10/2008 | Crescenzi et al. | |
| 2001/0018438 A1 | * | 8/2001 | Collins et al. .............. | 514/252.1 |
| 2004/0058945 A1 | | 3/2004 | Chaudhari et al. | |
| 2005/0025774 A1 | | 2/2005 | Crescenzi et al. | |
| 2007/0293464 A1 | | 12/2007 | Martin et al. | |
| 2008/0275004 A1 | | 11/2008 | Crescenzi et al. | |
| 2009/0005560 A1 | | 1/2009 | Oka et al. | |

FOREIGN PATENT DOCUMENTS

| | | | |
|---|---|---|---|
| JP | 2001-521924 A | | 11/2001 |
| JP | 2004-196772 A | | 7/2004 |
| JP | 2006-508133 A | | 3/2006 |
| JP | 2007-519735 A | | 7/2007 |
| RU | 2288227 C2 | | 11/2006 |
| WO | 9825905 A2 | | 6/1998 |
| WO | 9855480 A1 | | 12/1998 |
| WO | 9923075 A1 | | 5/1999 |
| WO | WO 9923075 A1 | * | 5/1999 |
| WO | 2004043927 A1 | | 5/2004 |
| WO | 2005074513 A2 | | 8/2005 |

OTHER PUBLICATIONS

Moore et. al., Journal of Organic Chemistry, 1967, American Chemical Society, vol. 32, pp. 1353-1360.*
Mulder et. al., Journal of the American College of Cardiology, 1997, American College of Cardiology, vol. 29, pp. 416-421.*
Rosenstock et. al., Pain, 2004, Elsevier, vol. 110, pp. 628-638.*
Eisert et. al., CAS STN Abstract, RN 60227-59-0, pub. 1976.*
Ried et. al., CAS STN Abstract, RN 23818-10-2, pub. 1969.*
Bonnelli et. al., Expert Opinion on Pharmacotherapy, 2007, Taylor & Francis Group, vol. 8, iss. 2, pp. 141-153.*
Chertkow et. al., Canadian Medical Association Journal, 2008, Canadian Medical Association, vol. 178, No. 10, pp. 1273-1285.*
Graziano et. al., Current Neurology & Neuroscience Reports, 2009, Current Medicine Group LLC, vol. 9, pp. 423-429.*
Imarisio et. al., Biochemical Journal, 2008, Biochemical Society, vol. 412, pp. 191-209.*
Mattox et. al., Child & Adolescent Social Work Journal, 2007, Springer Science, vol. 24, No. 2, pp. 195-207.*

(Continued)

*Primary Examiner* — Sarah Pihonak
(74) *Attorney, Agent, or Firm* — Fox Rothschild LLP; Gerard P. Norton; Jin Zhu

(57) ABSTRACT

The present invention relates to 4-pyridinone compounds which are inhibitors of catechol O-methyltransferase (COMT), and are useful in the treatment and prevention of neurological and psychiatric disorders and diseases in which COMT enzyme is involved. The present invention also relates to pharmaceutical compositions comprising these compounds and the use of these compounds and compositions in the prevention or treatment of such diseases in which COMT is involved.

16 Claims, No Drawings

(56) References Cited

OTHER PUBLICATIONS

Mosimann et. al., Swiss Medical Weekly, 2003, Swiss Medical Publishers, vol. 133, pp. 131-142.*
Lozano et. al., Scientific American, Jul. 2005, Nature Publishing Group, pp. 68-75.*
Tasman et al., Psychiatry, West Sussex, John Wiley & Sons, Ltd. Second Edition, vol. 1 (2003) pp. 254-272.
Sadock and Sadock et al., Kaplan & Sadock's Comprehensive Textbook of Psychiatry, 7th Edition, vol. 1 (2005) Philadelphia PA; Lippincott Williams & Wilkins pp. 236-272 and 1330-1395.
Okubo et al., Letters to Nature, vol. 385 (1997) pp. 634-636.
Carter, et al., The American Journal of Psychiatry (1998) vol. 115, pp. 1281-1284.
Williams, et al., Human Molecular Genetics, vol. 12 (2003), Review Issue 2, pp. R125-R133.
Takahashi et al., The Journal of Bone & Joint Surgery, vol. 85-A, No. 1, pp. 122-125 (2003).
Tunbridge et al., Biol. Psychiatry, vol. 60 pp. 141-151 (2006).
Chen et al., Biological Psychiatry, vol. 49, pp. 13-16 (2004).
Smiley et al., Proc. Natl. Acad. Sci. USA, vol. 91, pp. 5720-5724 (1994).
Sesack et al., Cerebral Cortex, pp. 614-622 (1998).
Lewis et al., Am. J. Psychiatry, vol. 158, pp. 1411-1422 (2001).
Moron et al., The Journal of Neuroscience, vol. 22(2), pp. 389-395 (2002).
Mazei et al., Brain Research, vol. 936, pp. 58-67, (2002).
Boulton et al., Advances in Pharmacology vol. 42, pp. 273-292 (1998).
Barch et al., Arch. Gen. Psychiatry vol. 58, pp. 280-288 (2001).
Callicott et al., Cerebral Cortex, vol. 10, pp. 1078-1092 (2000).
Abi-Dargham et al., The Journal of Neuroscience, vol. 22(9) pp. 3708-3719 (2002).
Weinberger D., Arch. Gen. Psychiatry vol. 43, pp. 114-124 (1986).
Weinberger J., J. Neural Transm. vol. 69, pp. 265-275 (1987).
Weinberger, D., Mesocortical Dopaminergic Function, pp. 330-338 (1988).
Daniel et al., The Journal of Neuroscience, vol. 11(7) pp. 1907-1917 (1991).
Lieberman et al., The New England Journal of Medicine, vol. 353, No. 12, pp. 1209-1223 (2005).
Lachman et al., Pharmacogenetics, vol. 6, pp. 243-250 (1996).
Green, M. F., Am. J. Psychiatry, vol. 153 (1996) pp. 321-330.
Akil et al., Am. J. Psychiatry, vol. 156 (1999) pp. 1580-1589.
Addington et al., British Journal of Psychiatry, vol. 163 (1993) p. 6.
Delaney et al., "A [4+2] Cycloaddition Strategy to Pyridine Boronic Eater Derivatives" May 5, 2008, Organic Letters, vol. 10, No. 5, pp. 781-783 (Abstract only).
Khanfar et al., Discovery of Novel GSK-3beta Inhibitors with Potent in Vitro and in Vivo Activities and Excellent Brain Permeability Using Combined Ligand- and Structure-Based Virtual Screening: Nov. 17, 2010, J Med Chem, vol. 53, No. 24, pp. 8534-8545.
Moore et al., "Heterocyclic Studies. XXV. Rearrangements of a-Acyl-1,2-diazabbicyclo[3.2.0]-3-hepten-6-ones in Methanol and in Base" May 1, 1967, J of Organic Chem, vol. 32, No. 5, pp. 1353-1360.
Ashwort, P., "Electron Spin Resonance Studies of Azasemiquinone Free Radical Intermediates in the Oxidation of Hydroxypyridones," Tetrahedron (1975); 32:261-267.
Borchardt, Ronald T., "Catechol O-Methyltransferase, 4, In Vitro Inhibition by 3-Hydroxy-4-pyrones, 3-Hydroxy-2-pyridones, and 3-Hydroxy-4-pyridones," Journal of Medicinal Chemistry (1973); 16(5):581-583.
Davies et al., "Novel Heterocyclic Systems, Part 4: A simple, convenient synthesis of 3-hydroxypyridine-2-thione, and the preparation fo two novel tricyclic betaines," Tetrahedron Letters (1980); 21:2191-2194.
Delaney et al., "A [4+2] Cycloaddition Strategy to Pyridine Boronic Ester Derivatives," Organic Letters (2008) 10(5):781-783.
Eistert et al., "Synthesis and reactiosn of substituted pyrroline-2,3-diones with diazoalkanes," Liebigs Ann. Chem. (1976) pp. 1023-1030.
Fox et al., "Synthetic studies into 3-Hydroxy-2(1)-pyridinone based Hexadentate Metal (III) Ion Chelators," Synthetic communications (1998); 28(9):1563-1574.
Katritzky et al., "Novel Thermal and Photochemical Rearrangements of N-Subtituted 2-Pyridones," J. Chem. Soc., Commun. (1979); 395-396.
Moore et al., "Heterocyclic Studies, IX, Some Transformations of the 1,2-diazabicyclo[3,2,0]heptane system," J. Am. Chem. Soc. (1962); 84(15):3022-3023.
Orama et al., "Iron(III)-Chelating Properties of the Novel Catechol O-Methyltransferase Inhibitor Entacapone in Aqueous Solution," Journal of Pharmaceutical sciences (1997) 86(7):827-831.
Raxworthy et al, "The Inhibition of Catechol-O-Methyltransferase by 2,3-Dihydroxypyrdine," Biochemical Pharmacology (1983); 32(8):1361-1364.
Ried et al., "Reactions with Cyclobutendion IX, 3-Hydroxy-pyridones-(2) from Phenylcyclobutenedione and Enanines," Liebigs Ann. Chem. (1969) 725"230-233.
Samant, Bhupesh S., "Synthesis of 3-hydroxypyrid-2-ones from furfural for treatment against iron overload and iron deficiency," European Journal of Medicinal Chemistry (2008); 43:1978-1982.
Singh et al., "Novel cAMP PDE III Inhibitors: Imidazo[4,5-b]pyridin-2(-3H)-ones and Thiazolo[4,5-b]pyridin-2(3H)-ones and Their Analogs," J. Med. Chem. (1994) 37(2):248-254.
Streater et al., "Novel 3-Hydroxy-2(1H)-pyridinones. Synthesis, Iron (III)-Chelating Properties, and Biological Activity," J. Med. Chem (1990); 33:1749-1755.

* cited by examiner

INHIBITORS OF CATECHOL O-METHYL TRANSFERASE AND THEIR USE IN THE TREATMENT OF PSYCHOTIC DISORDERS

CROSS REFERENCE TO RELATED APPLICATIONS

This application is the National Stage of International Application No. PCT/US2011/026414 filed on Feb. 28, 2011, which claims the benefit under 35 U.S.C. 119(e) of U.S. Provisional Application No. 61/310,400, filed Mar. 4, 2010.

BACKGROUND OF THE INVENTION

The symptoms of schizophrenia are generally divided into three categories; positive, negative and cognitive. Positive symptoms include hallucinations, delusions and disorganized behavior while negative symptoms are characterized by a lack of pleasure and/or interest in life. Cognitive deficit includes difficulties in the organization of thoughts and prioritization of tasks. Patients with bipolar disorder generally display circular mood changes ranging from severe depression to severe mania with or without psychotic features. Schizophrenia and bipolar disorder are among the most severe forms of psychiatric disorders that elicit overlapping cognitive deficits (Tasman et al., Psychiatry, West Sussex, John Wiley & Sons, Ltd., Second Edition, Volume 1, 2003, pp 254-272; and Sadock and Sadock, Kaplan and Sadock's Comprehensive Textbook of Psychiatry, 7 ed., Vol. 1, 2005, Philadelphia, Pa.; Lippincott Williams & Wilkins, pp 236-272 and 1330-1395) and they tend to be chronic/progressive. In contrast to positive symptoms, the negative and cognitive symptoms of schizophrenia are thought to have a greater impact on long-term disability, treatment outcome and functional recovery (Addington and Addington, 1993; Green, 1996). Dissatisfaction with therapy is attributed to lack of efficacy or intolerable and unacceptable side affects. The side effects have been associated with significant metabolic, extrapyramidal, prolactic and cardiac adverse events. See, Lieberman et al., N. Engl. J. Med. (2005) 353:1209-1223.

While multiple pathways are believed to be involved in the pathogenesis of schizophrenia leading to negative and cognitive symptoms, much attention has focused on reduced dopamine neurotransmission in the prefrontal cortex (Weinberger, 1987; Weinberger et al., 1988; Akil et al., 1999). Evidence for reduced dopamine neurotransmission in the prefrontal cortex is supported by reduced regional cerebral blood flow or hypoactivation of the dorsolateral prefrontal cortex in schizophrenia patients (Weinberger et al., 1988; Daniel et al., 1991; Okubo et al., 1997; Abi-Dargham et al., 2002). Schizophrenia related prefrontal deficits, independent from treatment or psychotic state, have been correlated with poor performance in tasks of executive function (e.g. n-back or Wisconsin Card Sorting Test) that evaluate prefrontal engagement (Weinberger et al., 1986, 1988; Carter et al., 1998; Callicott et al., 2000; Barch et al., 2001). In addition to deficits in executive function, reduced dopamine neurotransmission in the prefrontal cortex is involved in several brain activities including; attention, hedonic activities, natural rewards, and biologic activities such as cell signaling. Therefore, a compound which selectively enhances dopamine neurotransmission within the prefrontal cortex may have therapeutic potential for the treatment of cognitive and negative symptoms.

Dopamine levels in the brain are determined by biosynthesis and release, as well as its rate of diffusion, reuptake, and degradation. Catechol-O-methyltransferase (COMT), is an important enzyme involved in the breakdown of dopamine in the cortex. COMT converts dopamine to 3-methoxytyramine and the dopamine metabolite dihydroxyphenylacetic acid (DOPAC) to homovanillic acid (HVA) (Boulton and Eisenhofer, 1998). In fact, COMT acts on a variety of biogenic catecholamines as well as catecholestrogens, dietary phytochemicals and ascorbic acid. In subcortical structures (e.g. striatum), dopaminergic signalling is primarily regulated by removal of dopamine from the synaptic cleft via rapid uptake by the dopamine transporter (DAT) and/or norepinephrine transporter (NET). Regulation of dopamine transmission in the prefrontal cortex is markedly different. DAT is less densely expressed in synapses within the prefrontal cortex where dopamine is eliminated by uptake through the NET, diffusion, or metabolism by COMT and monoamine oxidase (Mazei et al., 2002; Moron et al., 2002; Lewis et al., 2001; Sesack et al., 1998; Smiley et al., 1994). COMT inhibitors would therefore be predicted to selectively increase cortical dopaminergic signaling and thereby improve cognitive function.

The COMT gene is located in the chromosome 22q11.21 region which has been linked to schizophrenia, bipolar disorder, ADHD and substance dependency (Williams, et al. 2003 and Takahashi et al., 2003). There are two major isoforms of COMT, membrane-bound COMT (MB-COMT) is the predominant form involved in the degradation of synaptic frontal lobe dopamine in human brain (Lachman et al., Pharmacogenetics (1996). 6(3):243-250). The other form is soluble COMT (S-COMT) which is transcribed from a different promoter than MB-COMT and is otherwise identical to human MB-COMT minus 50 amino acids at the N-terminus of the protein. In humans, COMT activity is modulated by a single nucleotide polymorphism at Val158Met (MB-COMT). Due to differences in enzyme thermostability, homozygous Met carriers have lower COMT activity, heterozygotes exhibit intermediate activity and homozygous Val carriers have greater enzyme activity (Chen et al., 2004). Despite the differences observed in activity based on genotype, only a modest relationship between Val158Met genotype and cognitive performance has been demonstrated by meta-analysis in normal individuals, while no effect was observed in schizophrenia. Based on an inverted-U relationship thought to exist between dopamine receptor activation and prefrontal cortical functioning, these findings might be reconciled with the fact that disease state, along with multiple environmental and genetic factors, contribute to prefrontal efficiency and dopamine levels (reviewed in Tunbridge et al., Biol Psych, 2006).

Although clozapine, Zyprexa, Risperdal and other antipsychotic drugs have been useful for the treatment of positive and arguably the negative symptoms of schizophrenia and bipolar disorder, they have not been free from side effects such as agranulocytosis, sedation, weight gain, hyper-lipidemia and hyperglycemia, all of which limit their applications (Tasman et al., 2003; Sadock and Sadock 2005). Thus, there remains a need for medications that effectively treat negative symptoms and cognitive deficit, have no major side effects, and are effective in the treatment of schizophrenia, bipolar disorder, depression, substance dependency, and ADD/ADHD, etc. Such medications might also be used to reduce such symptoms when they occur as part of another psychiatric syndrome or when they are incidental to a neurological disorder.

SUMMARY OF THE INVENTION

The present invention relates to 2-pyridinone compounds which are inhibitors of catechol O-methyltransferase (COMT) enzyme, and are useful in the treatment and prevention of neurological and psychiatric disorders and diseases in which COMT is involved.

The present invention also relates to pharmaceutical compositions comprising these compounds and the use of these compounds and compositions in the prevention or treatment of such diseases in which COMT enzyme is involved.

The present invention further relates to a method of treating symptoms associated with a psychiatric disorder, comprising administration of a pharmacologically effective dose of a composition comprising a 2-pyridinone COMT inhibitor or a pharmaceutically acceptable salt thereof to a patient.

Still, the present invention relates to improving negative symptoms and cognitive deficit associated with schizophrenia, augmentation of the effects of anti-psychotics in treatment of positive symptoms of schizophrenia, in treatment of major depression, the depressive phase of bipolar disorder, DA deficiency-related diseases such as ADD/ADHD, and substance dependency (combat cravings associated with and/or addictions to abuse of alcohol, opiates, cocaine, marijuana, amphetamines, tobacco). The present invention also relates to a method for the treatment of tobacco addiction and the weight gain/food cravings associated with quitting smoking or the use of antipsychotics.

The present invention also relates to a method of enhancing cognition in head injuries and dementias.

These and other aspects of the invention will be realized upon closer inspection of the specification as a whole.

DETAILED DESCRIPTION OF THE INVENTION

The present invention relates to novel COMT inhibitors of formula I

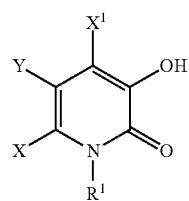

I including tautomers or pharmaceutically acceptable salts and individual enantiomers and diastereomers thereof wherein:
Y represents hydrogen, CN, $C_{2-6}$ alkynyl, $(CH_2)_nC_{5-10}$ heterocyclyl, $(CH_2)_nC_{6-10}$ aryl, said alkynyl, heterocyclyl and aryl optionally substituted with 1 to 3 groups of $R^a$;
X, $X^1$, and $R^1$ independently represent hydrogen, halo, CN, $C_{1-6}$ alkyl, $C_{2-6}$ alkynyl, $(CH_2)_nC_{6-10}$ aryl, $(CH_2)_nC_{5-10}$ heterocyclyl, said alkyl, heterocyclyl, and aryl optionally substituted with 1 to 3 groups of $R^a$;
$R^2$ represents H, OH, $C_{1-6}$ alkyl, $N(CH_3)_2$, $(CH_2)_nC_{3-10}$ cycloalkyl, $(CH_2)_nC_{5-10}$ heterocyclyl, $(CH_2)_nC_{6-10}$ aryl, said aryl and heterocyclyl optionally substituted with 1 to 3 groups of $R^a$;
$R^a$ represents $C_{1-6}$ alkyl, halogen, hydroxyl, $C_{2-4}$alkynyl, $(CH_2)_nCF_3$, $OCHF_2$, $OCF_3$, $C_{3-6}$ cycloalkyl, $NR^2C(O)R^2$, $C(O)N(R^2)_2$, $C(R^2)_2OR^2$, $C(O)R^2$, $NO_2$, CN, $N(R^2)_2$, $(CH_2)_nC(O)OR^2$, $SO_2R^2$, $NHSO_2R^2$, $OR^2$, $(CH_2)_nC_{5-10}$ heterocyclyl, $C(O)(CH_2)_nC_{5-10}$ heterocyclyl, $(CH_2)_nC_{6-10}$ aryl, or $C(O)(CH_2)_nC_{6-10}$ aryl, said alkyl, alkynyl, cycloalkyl, heterocyclyl and aryl optionally substituted with 1 to 3 groups of $R^b$;
$R^b$ represents $C_{1-6}$ alkyl, halogen, $CHF_2$, $OCHF_2$, —O—, $N(R^2)_2$, $CH_2OH$, $(CH_2)_nC_{6-10}$ aryl, $(CH_2)_nC_{5-10}$ heterocyclyl, $OR^2$, $C_{3-6}$cycloalkyl, $(CH_2)_nCF_3$, or CN; and
n represents 0 to 5.

An embodiment of the present invention is realized when Y is $(CH_2)_nC_{6-10}$ aryl, and all other variables are as originally described. A subembodiment of this invention is realized when Y is phenyl. Another subembodiment of this invention is realized when Y is napthyl.

An embodiment of the present invention is realized when Y is $(CH_2)_nC_{5-10}$ heterocyclyl, and all other variables are as originally described. A subembodiment of this invention is realized when Y is quinolinyl, A subembodiment of this invention is realized when Y is isoquinolinyl. Another subembodiment of this invention is realized when Y is thiazolyl. Another subembodiment of this invention is realized when Y is triazolyl. Another subembodiment of this invention is realized when Y is pyrrolyl. Another subembodiment of this invention is realized when Y is pyrrolidinyl. Another subembodiment of this invention is realized when Y is pyrazolyl. Another subembodiment of this invention is realized when Y is imidazolyl. Another subembodiment of this invention is realized when Y is pyrimidinyl.

An embodiment of the present invention is realized when Y is $C_{2-6}$ alkynyl, and all other variables are as originally described.

Still another embodiment of this invention is realized when $R^1$ is hydrogen an all other variables are as originally described.

Still another embodiment of this invention is realized when $R^1$ is optionally substituted $C_{1-6}$alkyl and all other variables are as originally described.

Another embodiment of this invention is realized when X and $X^1$ both are hydrogen and all other variables are as originally described.

Another embodiment of this invention is realized when X and $X^1$ both are hydrogen, R1 is hydrogen or optionally substituted $C_{1-6}$ alkyl, and Y is a substituted phenyl.

Yet another embodiment of this invention is realized when the $R^a$ substituent on Y is selected from the group consisting of $C_{1-6}$alkyl, $CF_3$, $OCF_3$, halo, CN, $NHSO_2R^2$, $NHC(O)R^2$, $C(O)N(R^2)_2$, $(CH_2)_nC_{6-10}$ aryl, $C(O)(CH_2)_nC_{6-10}$ aryl, $C_{5-10}$ heterocyclyl, $C(O)C_{5-10}$ heterocyclyl, $OC_{1-6}$alkyl, and $OC_{6-10}$aryl, said alkyl, aryl and heterocyclyl optionally substituted with 1 to 3 groups of $R^b$.

Another embodiment of this invention is realized when the $R^b$ substituent on the $R^a$ of Y is selected from the group consisting of halo, $C_{1-6}$alkyl, $OCHF_2$, and $CF_3$.

Still another embodiment of this invention is realized by structural formula Ia:

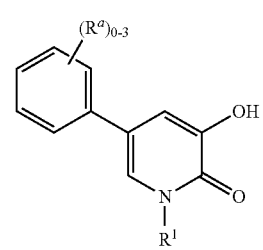

Ia including tautermer or pharmaceutically acceptable salts and individual enantiomers and diastereomers thereof wherein $R^1$ and $R^a$ are as previously described. A subembodiment of this invention is realized when $R^1$ is hydrogen or $C_{1-6}$ alkyl, and $R^a$ is selected from the group consisting of $C_{1-6}$alkyl, $CF_3$, $OCF_3$, halo, CN, $NHSO_2R^2$, $NHC(O)R^2$, $C(O)N(R^2)2$, $(CH_2)_nC_{6-10}$ aryl, $C(O)(CH_2)_nC_{6-10}$ aryl, $C_{5-10}$ heterocyclyl, $C(O)C_{5-10}$ heterocyclyl, $OC_{1-6}$alkyl, and $OC_{6-40}$aryl, said alkyl, aryl and heterocyclyl optionally substituted with 1 to 3 groups of $R^b$, and $R^2$ is as previously described. Another subembodiment of this invention is realized when $R^b$ is selected from the group consisting of halo, $C_{1-6}$alkyl, $OCHF_2$, and $CF_3$ Another subembodiment of the invention of structural formula Ia is realized wherein when $R^a$ is C(O) morpholinyl, CF3, OCF3, halo, C1-6 alkyl, CN, NHC(O)C1-6alkyl, oxadiazolyl, C(O)NHcyclohexyl, C2alkynyl, C(O) phenyl, C(O)benzoxazepinyl, said alyl, morpholinyl, oxadiazolyl, cyclohexyl, alkynyl, phenyl and benzoxazepinyl optionally substituted with 1 to 3 groups of $R^b$.

Still another embodiment of this invention is realized by structural formula Ib:

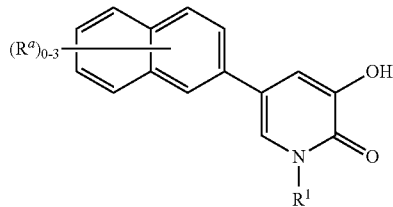

Ib including tautermer or pharmaceutically acceptable salts and individual enantiomers and diastereomers thereof wherein $R^1$ and $R^a$ are as previously described. A subembodiment of this invention is realized when $R^1$ is hydrogen or $C_{1-6}$ alkyl, and $R^a$ is selected from the group consisting of $C_{1-6}$alkyl, $CF_3$, $OCF_3$, halo, CN, $NHSO_2R^2$, $NHC(O)R^2$, $C(O)N(R^2)2$, $(CH_2)_nC_{6-10}$ aryl, $C(O)(CH_2)_nC_{6-10}$ aryl, $C_{5-10}$ heterocyclyl, $C(O)C_{5-10}$ heterocyclyl, $OC_{1-6}$alkyl, and $OC_{6-10}$aryl, said alkyl, aryl and heterocyclyl optionally substituted with 1 to 3 groups of $R^b$, and $R^2$ is as previously described. Another subembodiment of this invention is realized when $R^b$ is selected from the group consisting of halo, $C_{1-6}$alkyl, $OCHF_2$, and $CF_3$ Another subembodiment of the invention of structural formula Ia is realized wherein when $R^a$ is C(O) morpholinyl, CF3, OCF3, halo, C1-6 alkyl, CN, NHC(O)C1-6alkyl, oxadiazolyl, C(O)NHcyclohexyl, C2alkynyl, C(O) phenyl, C(O)benzoxazepinyl, said alyl, morpholinyl, oxadiazolyl, cyclohexyl, alkynyl, phenyl and benzoxazepinyl optionally substituted with 1 to 3 groups of $R^b$.

Another embodiment of this invention is realized by structural formula Ic:

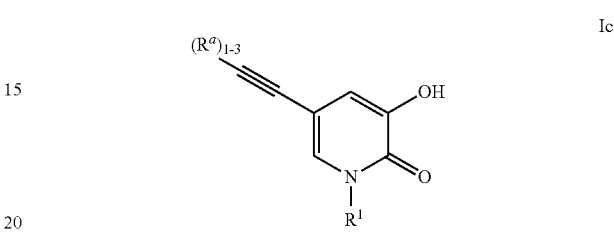

Ic including tautermer or pharmaceutically acceptable salts and individual enantiomers and diastereomers thereof wherein $R^1$ and $R^a$ are as previously described. A subembodiment of this invention is realized when $R^1$ is hydrogen or C1-6 alkyl, and $R^a$ is selected from the group consisting of $C_{1-6}$alkyl, $CF_3$, $OCF_3$, halo, CN, $NHSO_2R^2$, $NHC(O)R^2$, $C(O)N(R^2)2$, $(CH_2)_nC_{6-10}$ aryl, $C(O)(CH_2)_nC_{6-10}$ aryl, $C_{5-10}$ heterocyclyl, $C(O)C_{5-10}$ heterocyclyl, $OC_{1-6}$alkyl, and $OC_{6-10}$aryl, said alkyl, aryl and heterocyclyl optionally substituted with 1 to 3 groups of $R^b$, and $R^2$ is as previously described. Another subembodiment of this invention is realized when $R^b$ is selected from the group consisting of halo, $C_{1-6}$alkyl, $OCHF_2$, and $CF_3$ Another subembodiment of the invention of structural formula Ia is realized wherein when $R^a$ is C(O) morpholinyl, CF3, OCF3, halo, C1-6 alkyl, CN, NHC(O)C1-6alkyl, oxadiazolyl, C(O)NHcyclohexyl, C2alkynyl, C(O) phenyl, C(O)benzoxazepinyl, said alyl, morpholinyl, oxadiazolyl, cyclohexyl, alkynyl, phenyl and benzoxazepinyl optionally substituted with 1 to 3 groups of $R^b$.

Examples of compounds of this invention are found in Table 1:

| Compound# | Structure | IUPAC Name | Exact Mass [M + H]+ |
| --- | --- | --- | --- |
| 1 | 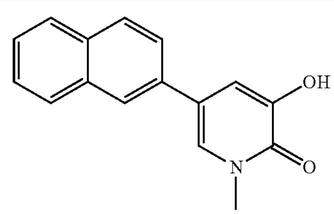 [SMILES: Cn1cc(-c2ccc3ccccc3c2)cc(O)c1=O] | 3-hydroxy-1-methyl-5-naphthalen-2-ylpyridin-2(1H)-one | Calc'd 252.1, found 252.1 |
| 2 | 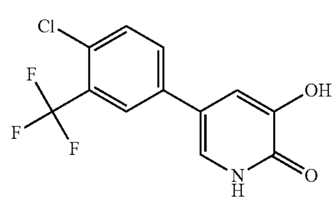 [SMILES: O=c1[nH]cc(-c2ccc(Cl)c(C(F)(F)F)c2)cc1O] | 5-[4-chloro-3-(trifluoromethyl)-phenyl]-3-hydroxypyridin-2(1H)-one | Calc'd 290.0, found 290.0 |

-continued

Examples of compounds of this invention are found in Table 1:

| Compound# | Structure | IUPAC Name | Exact Mass [M + H]+ |
|---|---|---|---|
| 3 | 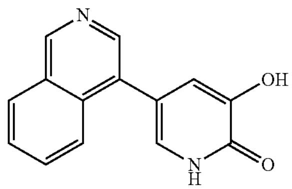 [SMILES: O=c1[nH]cc(-c2cncc3ccccc23)cc1O] | 3-hydroxy-5-(isoquinolin-4-yl)pyridin-2(1H)-one | Calc'd 239.1, found 239.1 |
| 4 | 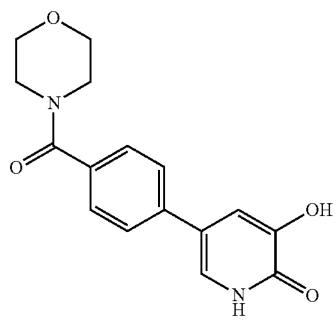 [SMILES: O=C(c1ccc(-c2c[nH]c(=O)c(O)c2)cc1)N1CCOCC1] | 3-hydroxy-5-[4-(morpholin-4-ylcarbonyl)phenyl]pyridin-2(1H)-one | Calc'd 301.1, found 301.1 |
| 5 | 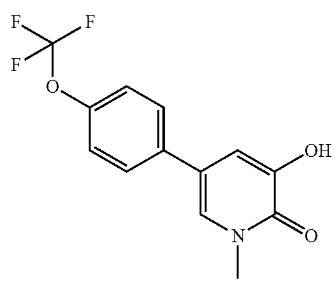 [SMILES: Cn1cc(-c2ccc(OC(F)(F)F)cc2)cc(O)c1=O] | 3-hydroxy-1-methyl-5-[4-(trifluoromethoxy)phenyl]pyridin-2(1H)-one | Calc'd 286.1, found 286.1 |
| 6 | 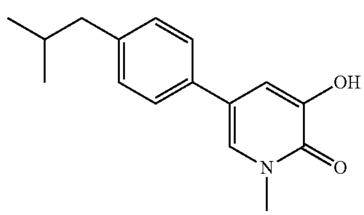 [SMILES: CC(C)Cc1ccc(-c2cc(O)c(=O)n(C)c2)cc1] | 3-hydroxy-1-methyl-5-[4-(2-methylpropyl)phenyl]pyridin-2(1H)-one | Calc'd 258.1, found 258.1 |
| 7 | 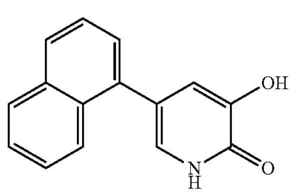 [SMILES: O=c1[nH]cc(-c2cccc3ccccc23)cc1O] | 3-hydroxy-5-(naphthalen-1-yl)pyridin-2(1H)-one | Calc'd 238.1, found 238.1 |
| 8 | 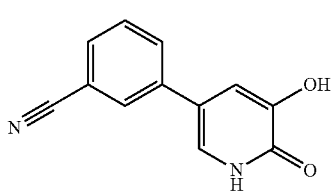 [SMILES: N#Cc1cccc(-c2c[nH]c(=O)c(O)c2)c1] | 3-(5-hydroxy-6-oxo-1,6-dihydropyridin-3-yl)benzonitrile | Calc'd 213.1, found 213.1 |

-continued

Examples of compounds of this invention are found in Table 1:

| Compound# | Structure | IUPAC Name | Exact Mass [M + H]+ |
|---|---|---|---|
| 9 | 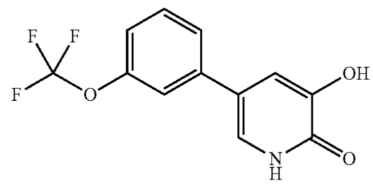 [SMILES: O=c1[nH]cc(-c2cccc(OC(F)(F)F)c2)cc1O] | 3-hydroxy-5-[3-(trifluoromethoxy)phenyl]pyridin-2(1H)-one | Calc'd 272.1, found 272.1 |
| 10 | 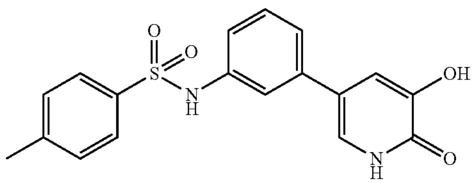 [SMILES: Cc1ccc(S(=O)(=O)Nc2cccc(-c3c[nH]c(=O)c(O)c3)c2)cc1] | N-[3-(5-hydroxy-6-oxo-1,6-dihydropyridin-3-yl)phenyl]-4-methylbnezene-sulfonamide | Calc'd 357.1, found 357.1 |
| 11 | 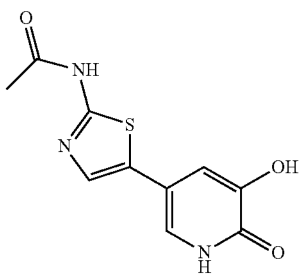 [SMILES: CC(=O)Nc1ncc(-c2c[nH]c(=O)c(O)c2)s1] | N-[5-(5-hydroxy-6-oxo-1,6-dihydropyridin-3-yl)-1,3-thiazol-2-yl]acetamide | Calc'd 252.0, found 252.0 |
| 12 | 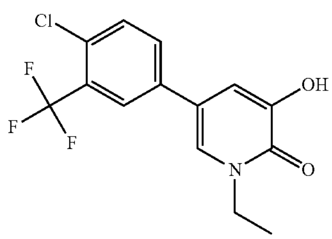 [SMILES: CCn1cc(-c2ccc(Cl)c(C(F)(F)F)c2)cc(O)c1=O] | 5-[4-chloro-3-(trifluoromethyl)phenyl]-1-ethyl-3-hydroxypyridin-2(1H)-one | Calc'd 318.1, found 318.1 |
| 13 | 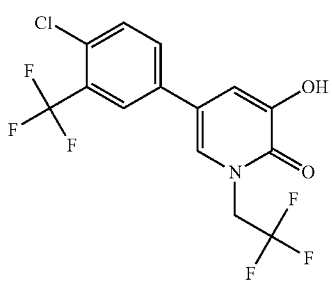 [SMILES: O=c1c(O)cc(-c2ccc(Cl)c(C(F)(F)F)c2)cn1CC(F)(F)F] | 5-[4-chloro-3-(trifluoromethyl)phenyl]-3-hydroxy-1-(2,2,2-trifluoroethyl)pyridin-2(1H)-one | Calc'd 372.0, found 372.0 |
| 14 | 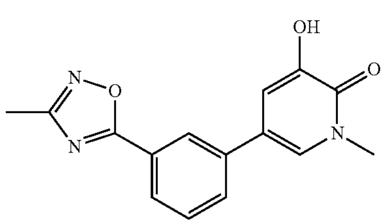 [SMILES: Cc1noc(-c2cccc(-c3cc(O)c(=O)n(C)c3)c2)n1] | 5-[3-(3-methyl-1,2,4-oxadiazol-5-yl)phenyl]pyridin-2(1H)-one | Calc'd 284.1, found 284.1 |

-continued

Examples of compounds of this invention are found in Table 1:

| Compound# | Structure | IUPAC Name | Exact Mass [M + H]+ |
|---|---|---|---|
| 15 | 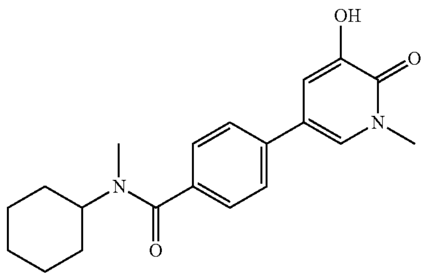 [SMILES: CN(C(=O)c1ccc(-c2cc(O)c(=O)n(C)c2)cc1)C1CCCCC1] | N-cyclohexyl-4-(5-hydroxy-1-methyl-6-oxo-1,6-dihydropyridin-3-yl)-N-methylbenzamide | Calc'd 341.2, found 341.2 |
| 16 | 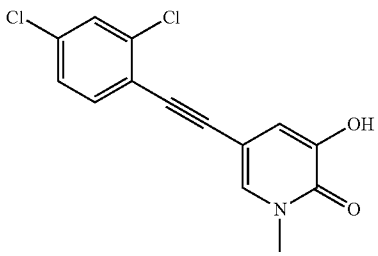 [SMILES: Cn1cc(C#Cc2ccc(Cl)cc2Cl)cc(O)c1=O] | 5-[(2,4-diclorophenyl)ethynyl]-3-hydroxy-1-methylpyridin-2(1H)-one | Calc'd 294.0, found 294.0 |
| 17 | 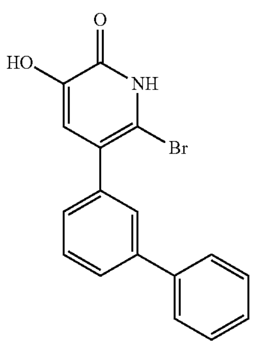 [SMILES: O=c1[nH]c(Br)c(-c2cccc(-c3ccccc3)c2)cc1O] | 5-biphenyl-3-yl-6-bromo-3-hydroxypyridin-2(1H)-one | Calc'd 342.0, found 342.0 |
| 18 | 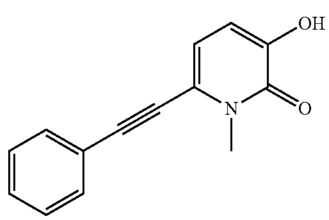 [SMILES: Cn1c(C#Cc2ccccc2)ccc(O)c1=O] | 3-hydroxy-1-methyl-6-(phenylethynyl)pyridin-2(1H)-one | Calc'd 226.1, found 226.1 |
| 19 | 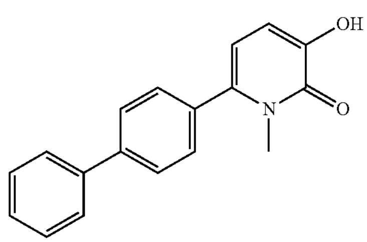 [SMILES: Cn1c(-c2ccc(-c3ccccc3)cc2)ccc(O)c1=O] | 6-biphenyl-4-yl-3-hydroxy-1-methylpyridin-2(1H)-one | Calc'd 278.1, found 278.1 |
| 20 | 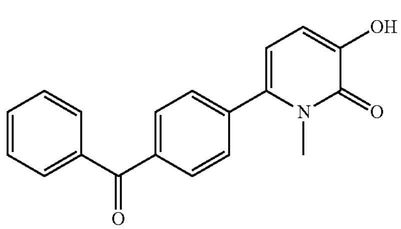 [SMILES: Cn1c(-c2ccc(C(=O)c3ccccc3)cc2)ccc(O)c1=O] | 6-[4-(phenylcarbonyl)phenyl]pyridin-2(1H)-one | Calc'd 306.1, found 306.1 |

| Compound# | Structure | IUPAC Name | Exact Mass [M + H]+ |
|---|---|---|---|
| 21 | 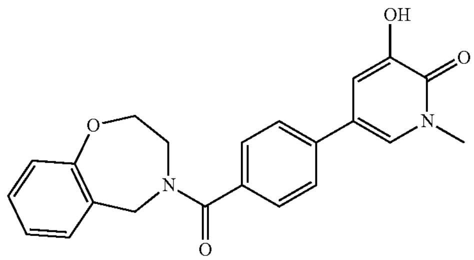 [SMILES: Cn1cc(-c2ccc(C(=O)N3CCOc4ccccc4C3)cc2)cc(O)c1=O] | 5-[4-(2,3-dihydro-1,4-benzoxazepin-4(5H)-ylcarbonyl)phenyl]-3-hydroxy-1-methylpyridin-2(1H)-one | Calc'd 377.1, found 377.1 |
| 22 | 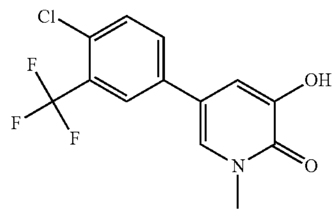 [SMILES: Cn1cc(-c2ccc(Cl)c(C(F)(F)F)c2)cc(O)c1=O] | 5-[4-chloro-3-(trifluoromethyl)phenyl]-3-hydroxy-1-methylpyridin-2(1H)-one | Calc'd 304.0, found 304.0 |
| 23 | | 6-(3,4-dichlorophenyl)-3-hydroxy-1-methylpyridin-2(1H)-one | Calc'd 270.0, found 270.0 | including tautomers or pharmaceutically acceptable salts and individual enantiomers and diastereomers thereof.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

In addition, the compounds disclosed herein may exist as tautomers and both tautomeric forms are intended to be encompassed by the scope of the invention, even though only one tautomeric structure is depicted. For example, any claim to compound A below is understood to include tautomeric structure B and vice versa, as well as mixtures thereof.

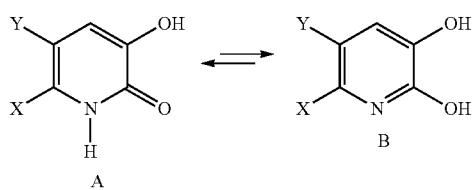

When R is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyls are $C_2$-$C_6$ alkynyl.

"Alkenyl," "alkynyl" and other like terms include carbon chains containing at least one unsaturated C—C bond.

As used herein, "fluoroalkyl" refers to an alkyl group as described herin containing at least one fluorine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl.

In certain other embodiments, the heterocyclic group is fused to an aryl or heteroaryl group. Examples of such fused heterocycles include, without limitation, tetrahydroquinolinyl and dihydrobenzofuranyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

Examples of heterocycloalkyls include azetidinyl, pyrrolidinyl, piperidinyl, piperazinyl, morpholinyl, tetrahydrofuranyl, imidazolinyl, pyrrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4-fluor-3-propylphenyl. As another non-limiting example, substituted n-octyls include 2,4dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfnyl, arylsulfnyl, $C_1$-$C_8$ alkylsulfonyl, aralkylsulfonyl, arylsulfonyl, $C_0$-$C_6$ N-alkylcarbamoyl, $C_2$-$C_{15}$ N,N' dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" or "halo" refers to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

The phrases "effective amount" or "therapeutically effective amount" mean a concentration of COMT enzyme complex modulator sufficient to inhibit or enhance the effect of the COMT enzyme complex.

"Treating" or "treatment of" a disease state includes: 1) inhibiting the disease state, i.e., arresting the development of the disease state or its clinical symptoms; 2) or relieving the disease state, i.e., causing temporary or permanent regression of the disease state or its clinical symptoms.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amities and substituted amities such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temperal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders. In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain. In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The subject compounds are further useful in a method for the prevention, treatment, control, amelioration, or reduction of risk of the diseases, disorders and conditions noted herein.

In another specific embodiment, compounds of the present invention provide a method for treating Parkinson's disease when co-administered with L-DOPA, with or without a aromatic L-amino acid decarboxylase inhibitor (AADC) such as carbidopa, by preventing COMT-mediated metabolism of L-DOPA.

The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, other COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

COMT inhibitor drugs have a beneficial effect in ill individuals if the principle or minor cause of illness is due to frontal lobe hypodopaminergia for multiple reasons, including, but not limited to, COMT over activity. COMT inhibitors are expected to be more useful in individuals with hypomethylated MB-COMT promoter and/or Val/Val and Val/Met genotype than those with Met/Met genotype.

The medicinal products which are useful in the treatment of these diseases consist of COMT inhibitor drugs or MB-COMT inhibitors or a pharmaceutical salt thereof either alone or in the form of a composition in which it is combined with any other pharmaceutically compatible product, which may be inert or physiologically active. These medicinal products may be used orally, topically, parenterally or rectally.

In addition to primates, such as humans, a variety of other mammals can be treated according to the method of the present invention. For instance, mammals including, but not limited to, cows, sheep, goats, horses, dogs, cats, guinea pigs, or other bovine, ovine, equine, canine, feline, or rodent, such as mouse, species can be treated. However, the method can also be practiced in other species, such as avian species (e.g., chickens).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

Further, it is understood that compounds of this invention can be administered at prophylactically effective dosage levels to prevent the above-recited conditions and disorders, as well as to prevent other conditions and disorders associated with calcium channel activity.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, and dusting powder. Further, the compositions can be in a form suitable for use in transdermal devices. These formulations may be prepared, utilizing a compound represented of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound of the invention, or pharmaceutically acceptable salts thereof, can also be prepared in powder or liquid concentrate form.

The abbreviations used herein have the following meanings (abbreviations not shown here have their meanings as commonly used unless specifically stated otherwise): Ac (acetyl), Bn (benzyl), Boc (tertiary-butoxy carbonyl), Bop reagent (benzotriazol-1-yloxy)tris(dimethylamino)phosonium hexafluorophosphate, DBU (1,8-diazabicyclo[5.4.0] undec-7-ene), LHMDS (lithium hexamethyldisilyl amide), DMSO (methyl sulfoxide), PPTS (pridinium p-toluenesulfonate), PD/C (palladium on carbon), HRMS high resolution mass spectrometry, DCM (dichloromethane), LDA (lithium diisopropylamide), HPLC (high performance liquid chromatography) DIPEA (diisopropylethyl amine), DMAP (4-(dimethylamino)pyridine), NMR (nuclear magnetic resonance); DMF (N,N-dimethylformamide), EDC (1-(3-dimethylaminopropyl)-3-ethylcarbodiimide hydrochloride), $Et_3N$ (triethylamine), GST (glutathione transferase), HOBt (1-hydroxybenzotriazole), LAH (lithium aluminum hydride), Ms (methanesulfonyl; mesyl; or $SO_2Me$), MsO (methanesulfonate or mesylate), NaHMDS (sodium hexamethyldisilazane), NBS (N-bromosuccinimide), NCS (N-chlorosuccinimide), NSAID (non-steroidal anti-inflammatory drug), PDE (Phosphodiesterase), Ph (Phenyl), r.t. or RT (room temperature), Rac (Racemic), SAM (aminosulfonyl; sulfonamide or $SO_2NH_2$), SPA (scintillation proximity assay), Th (2- or 3-thienyl), TFA (trifluoroacetic acid), THF (Tetrahydrofuran), TLC (thin layer chromatography), Tr or trityl (N-triphenylmethyl), $C_3H_5$ (Allyl), Me (methyl), Et (ethyl), n-Pr (normal propyl), i-Pr (isopropyl), n-Bu (normal butyl), i-Butyl (isobutyl), s-Bu (secondary butyl), t-Bu (tertiary butyl), c-Pr (cyclopropyl), c-Bu (cyclobutyl), c-Pen (cyclopentyl), c-Hex (cyclohexyl).

The present compounds can be prepared according to the procedures provided in the Examples. The following Examples further describe, but do not limit, the scope of the invention.

Unless specifically stated otherwise, the experimental procedures were performed under the following conditions: All operations were carried out at room or ambient temperature; that is, at a temperature in the range of 18-25° C. Inert gas protection was used when reagents or intermediates were air and moisture sensitive. Evaporation of solvent was carried out using a rotary evaporator under reduced pressure (600-4000 pascals: 4.5-30 mm Hg) with a bath temperature of up to 60° C. The course of reactions was followed by thin layer chromatography (TLC) or by high-pressure liquid chromatography-mass spectrometry (HPLC-MS), and reaction times are given for illustration only. The structure and purity of all final products were assured by at least one of the following techniques: TLC, mass spectrometry, nuclear magnetic resonance (NMR) spectrometry or microanalytical data. When given, yields are for illustration only. When given, NMR data is in the fowl of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The procedures described herein for synthesizing the compounds may include one or more steps of protecting group manipulations and of purification, such as, re-crystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1H$ and $^{13}C$ NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g. toluene, xylenes), halogenated solvents (e.g. methylene chloride, chloroform, carbontetrachloride, chlorobenzenes), ethers (e.g. diethyl ether, diisopropylether, tert-butyl methyl ether, diglyme, tetrahydrofuran, dioxane, anisole), nitriles (e.g. acetonitrile, propionitrile), ketones (e.g. 2-butanone, diethyl ketone, tert-butyl methyl ketone), alcohols (e.g. methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, alkyl magnesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the examples below can be further manipulated, when appropriate, using the standard functional group transformation techniques available to those skilled in the art, to provide desired compounds described in this invention.

It is also understood that compounds of this invention contain one or more stereocenters that may be prepared as single enantiomers or diastereomers, or as mixtures containing two or more enantiomers or diastereomers in any proportion.

Other variations or modifications, which will be obvious to those skilled in the art, are within the scope and teachings of this invention. This invention is not to be limited except as set forth in the following claims.

Several methods for preparing the compounds of this invention are illustrated in the following Schemes and Examples. Starting materials are made according to procedures known in the art or as illustrated herein.

REACTION SCHEMES

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

GENERAL REACTION SCHEMES
Scheme 1
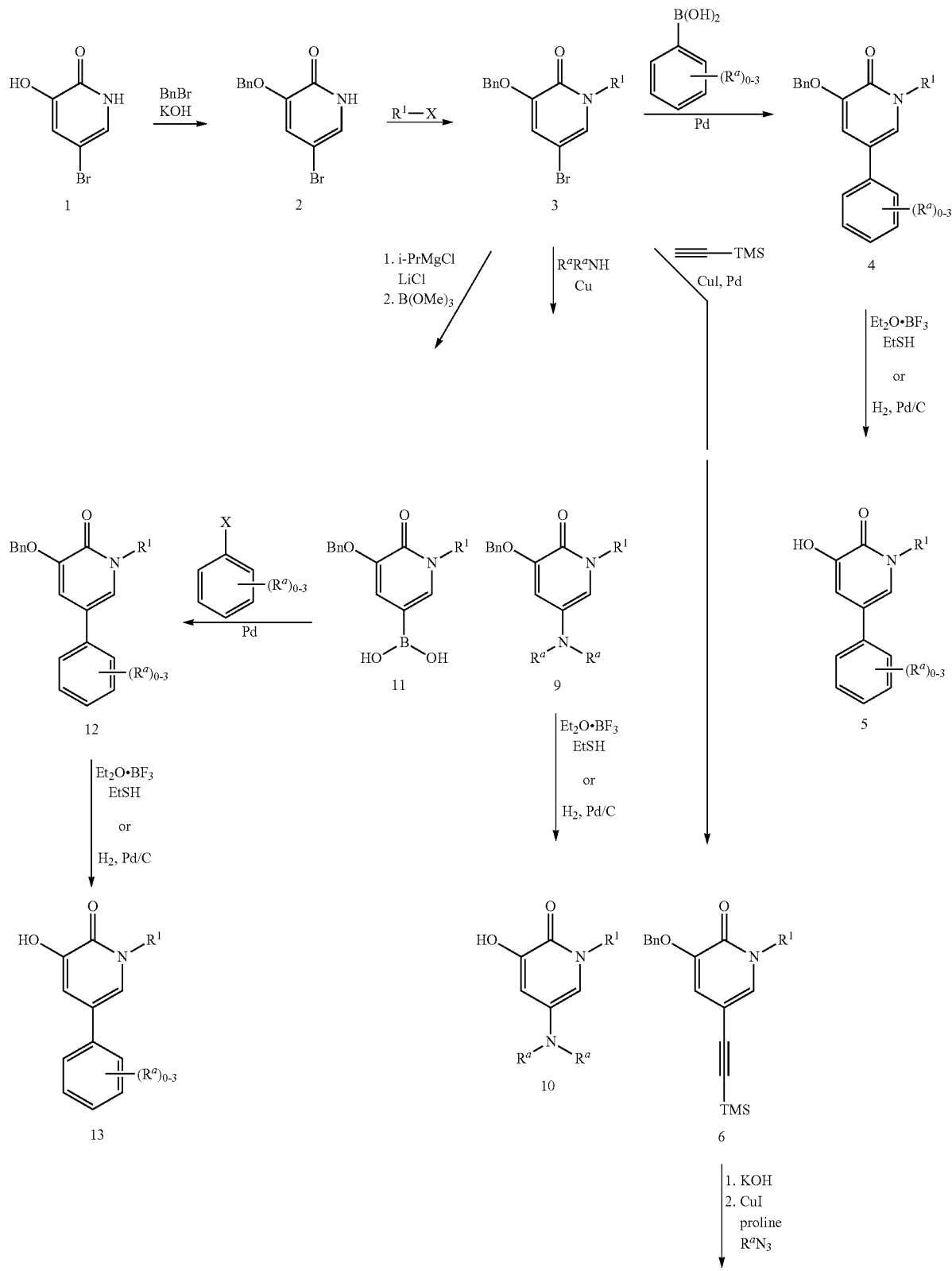

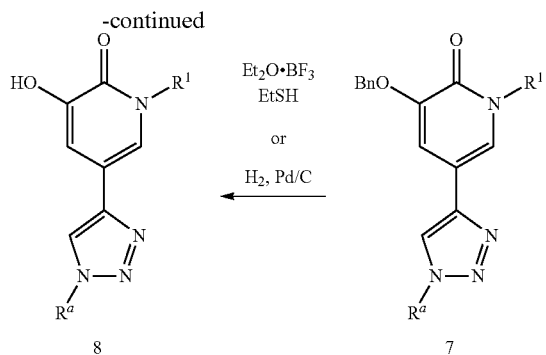

Compounds of the invention may be prepared as outlined in Scheme 1. Bromopyridine 1 is protected and N-alkylated with introduction of substituent $R^1$ to provide pyridinones 3. Compounds 3 are cross coupled to incorporate aryl and heteroaryl substituents and the resulting biaryls are deprotected to afford target compounds 5. Alternatively, compounds 3 are converted to alkynes 6 under Pd catalysis and subjected to Cu-catalyzed [3+2] cycloaddition with substituted azides to generate triazoles 7, which are deprotected to provide target compounds 8. Alternatively, compounds 3 are to N-arylated and deprotected to furnish target compounds 10. Alternatively, compounds 3 are converted to their corresponding boronic acids 11 before being cross coupled to aryl and heteroaryl halides and deprotected to provide target compounds 13. Compounds of Scheme 1 can be further modified by manipulation of the substitutent groups by general methods known in the art, including (but not limited to) cross coupling, oxidation, reduction, dealkylation, alkylation, acylation, and the like, and this modification may occur prior to or after deprotection.

Scheme 2

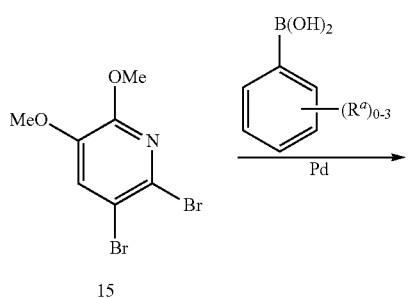

14

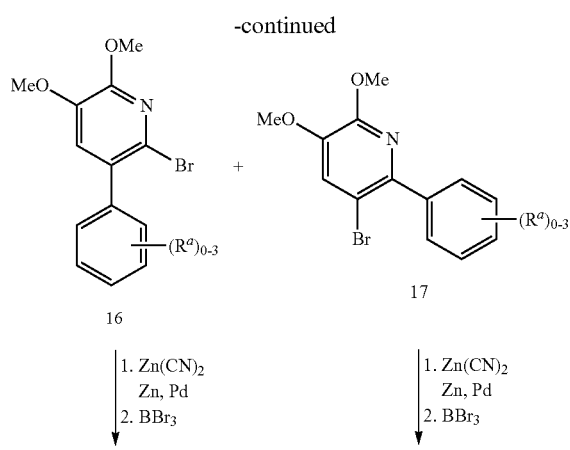

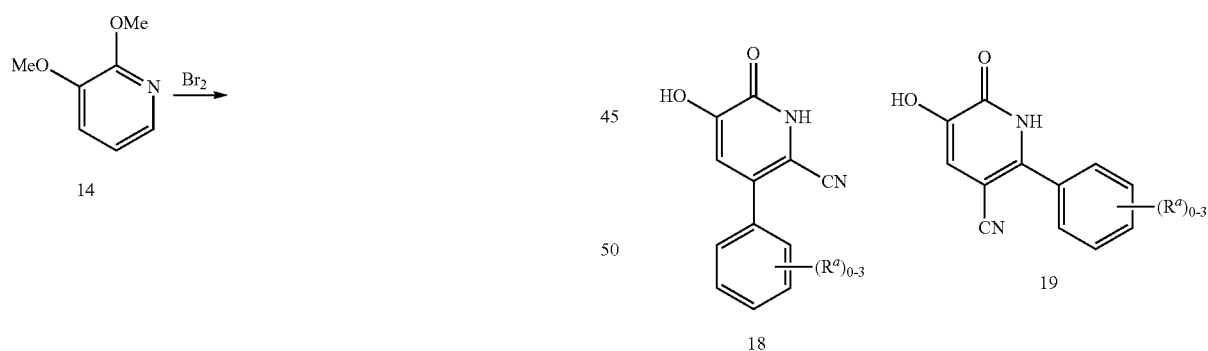

Compounds of the invention may be prepared as outlined in Scheme 2. Bromination of dimethoxypyridine 14 and Pd catalyzed arylation with substituted boronic acids provides mixtures of compounds 16 and compounds 17 which are separated and subjected to Pd and Zn mediated cyanation and deprotection to furnish target compounds 18 and 19. Compounds of Scheme 2 can be further modified by manipulation of the substitutent groups by general methods known in the art, including (but not limited to) cross coupling, oxidation, reduction, dealkylation, alkylation, acylation, and the like, and this modification may occur prior to or after deprotection.

Scheme 3

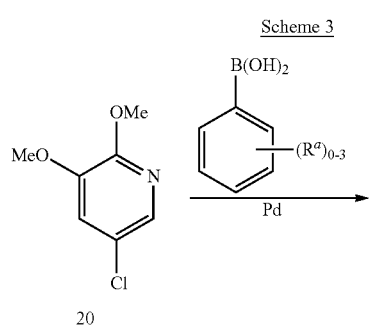

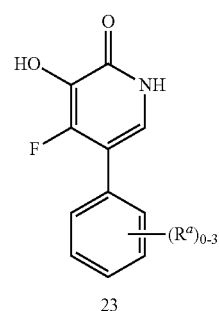

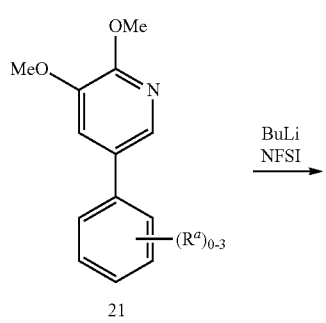

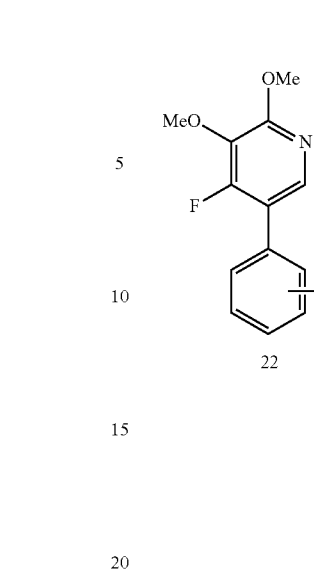

Compounds of the invention may be prepared as outlined in Scheme 3. Dimethoxypyridine 20 is converted to biaryls 21 prior to lithiation and fluorination to provide compounds 22. These intermediates are deprotected to provide target compounds 23 or, alternatively, protected as benzyl ethers, N-alkylated with introduction of substituent $R^1$, and deprotected to furnish target compounds 24. Compounds of Scheme 3 can be further modified by manipulation of the substitutent groups by general methods known in the art, including (but not limited to) cross coupling, oxidation, reduction, dealkylation, alkylation, acylation, and the like, and this modification may occur prior to or after deprotection.

Scheme 4

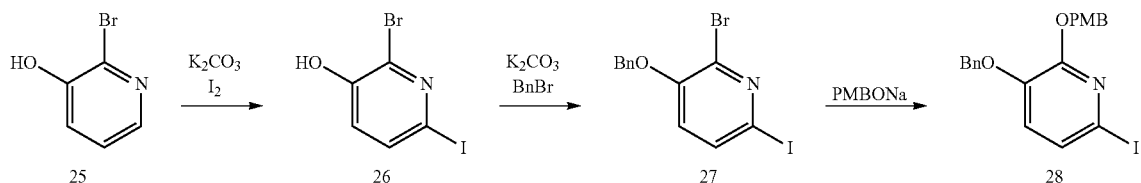

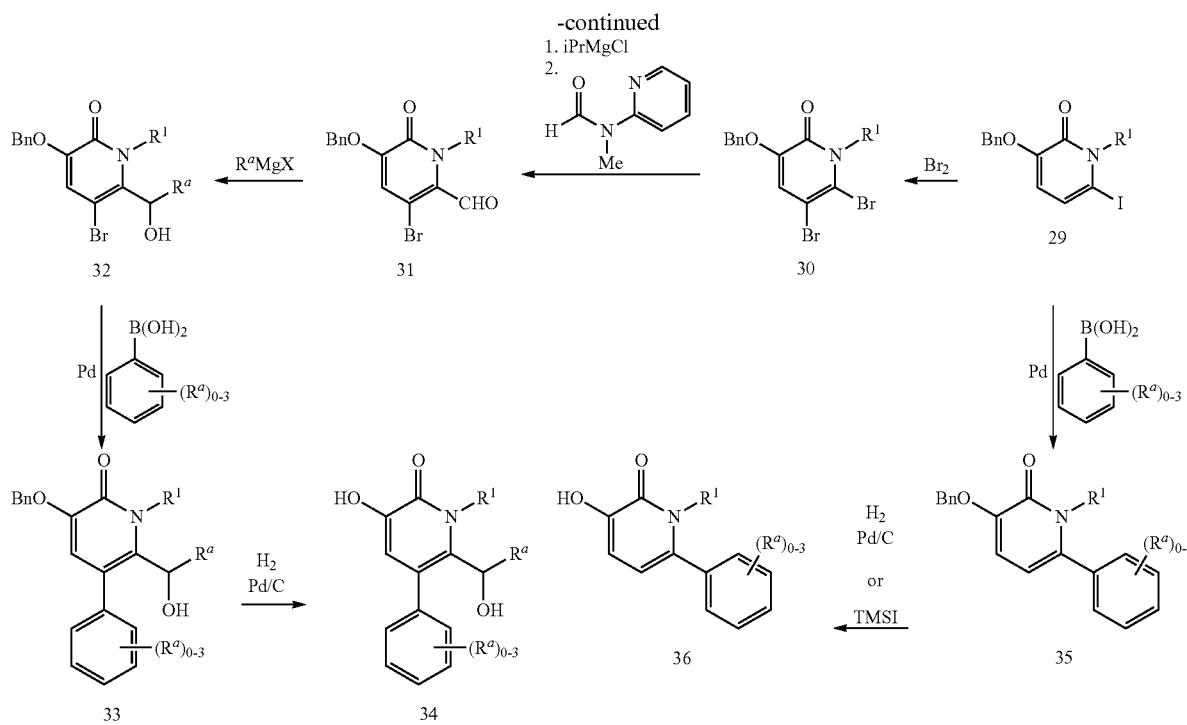

Compounds of the invention may be prepared as outlined in Scheme 4. Bromopyridine 25 is iodinated and protected prior to treatment with the sodium salt of p-methoxybenzyl alcohol to provide 28. p-Methoxybenzyl ether cleavage (TFA) and N-alkylation incorporates substituent $R^1$ and furnishes compounds 29 which, upon bromination and formylation generates compounds 31. Carbonyl addition of organometallic reagents provides compounds 32 which are cross coupled to substituted aryl and heteroaryl boronic acids and deprotected to furnish target compounds 34. Alternatively, compounds 29 are cross coupled to substituted aryl and heteroaryl boronic acids and deprotected to furnish target compounds 36. Compounds of Scheme 4 can be further modified by manipulation of the substituent groups by general methods known in the art, including (but not limited to) cross coupling, oxidation, reduction, dealkylation, alkylation, acylation, and the like, and this modification may occur prior to or after deprotection.

EXAMPLE 1

5-(2,4-Dichloro-phenyl)-3-hydroxy-1-methyl-1H-pyridin-2-one (1)

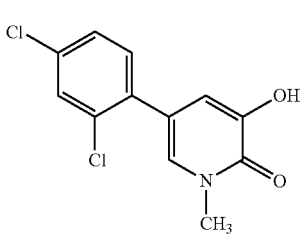

3-Benzyloxy-5-bromo-1H-pyridin-2-one

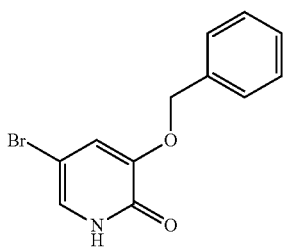 [SMILES: O=c1[nH]cc(Br)cc1OCc1ccccc1]

To a solution of 4.4 g (23.2 mmol) 5-bromo-3-hydroxy-1H-pyridin-2-one and 1.2 g (30 mmol) NaOH in 116 mL MeOH was added benzyl bromide dropwise at room temperature. The resulting mixture was heated to 60° C. overnight. After cooling, the volatiles were removed in vacuo, 20 mL water and 40 mL EtOAc were added, and the aqueous phase was extracted 2× with 20 mL EtOAc. The combined organics were dried over $Na_2SO_4$ and evaporated. Purification by automated flash chromatography (80 g silica gel cartridge 0-100%

EtAOc/hex over 30 min) afforded 2.51 g (38.7%) 3-benzy-loxy-5-bromo-1H-pyridin-2-one. LCMS [M+H]+=280.1

3-Benzyloxy-5-bromo-1-methyl-1H-pyridin-2-one

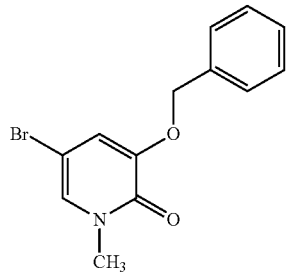 [SMILES: Cn1cc(Br)cc(OCc2ccccc2)c1=O]

To a suspension of 2.51 g (8.96 mmol) 3-benzyloxy-5-bromo-1H-pyridin-2-one and 2.48 g (17.9 mmol) $K_2CO_3$ in 45 mL DMF was added 1.12 mL (17.9 mmol) iodomethane at room temperature. After stirring overnight, 150 mL water was added with vigorous stirring causing precipitation of the product which was collected by filtration and dried in vacuo affording 2.3 g (87%) 3-benzyloxy-5-bromo-1-methyl-1H-pyridin-2-one
containing 10% of the O-methylated isomer by LCMS. Material was used in subsequent steps without further purification. $^1$H NMR (300 MHz, $CHCl_3$-d): δ 7.46-7.27 (m, 5 H); 7.05 (d, J=2.41 Hz, 1 H); 6.70 (d, J=2.42 Hz, 1 H); 5.10 (s, 2 H); 3.55 (s, 3 H). LCMS [M+H]+=294.1.

5-(2,4-Dichloro-phenyl)-3-hydroxy-1-methyl-1H-pyridin-2-one (1)

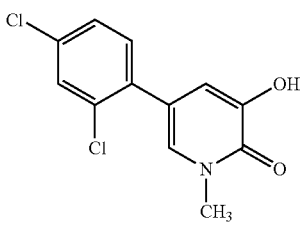

To a suspension of 0.045 (0.15 mmol) 3-benzyloxy-5-bromo-1-methyl-1H-pyridin-2-one, 0.44 g (0.23 mmol) 2,6-dichlorophenylboronic acid, and 0.006 g (0.008 mmol) dichloro 1,1'-bis(diphenylphosphino)ferrocene palladium (II) dichloromethane adduct in 2 mL THF was added 1 mL 1 M aq $Cs_2CO_3$. The resulting mixture was microwaved to 160° C. for 10 min. After cooling, the organic phase was separated and concentrated and the resulting residue was re-dissolved in MeOH. 0.02 mg (0.019 mmol) 10% Pd/C was added and the resulting suspension was stirred under 1 atm hydrogen gas overnight. The reaction mixture was filtered and concentrated. Purification by automated mass-guided HPLC afforded 0.045 g (11%) 5-(2,4-dichloro-phenyl)-3-hydroxy-1-methyl-1H-pyridin-2-one. $^1$H NMR (499 MHz, DMSO-$d_6$): δ 9.29 (s, 1 H); 7.71 (d, J=2.13 Hz, 1 H); 7.48 (dd, J=8.32, 2.19 Hz, 1 H); 7.43 (d, J=8.30 Hz, 1 H); 7.34 (d, J=2.35 Hz, 1 H); 6.82 (d, J=2.35 Hz, 1 H); 3.53 (s, 3 H). High resolution mass spec (FT/ICR) calc (M+H)+=270.0084 found 270.0083.

EXAMPLE 2

5-[4-Chloro-3-(trifluoromethyl)phenyl]-3-hydroxy-1-(propan-2-yl)pyridin-2(1H)-one (2)

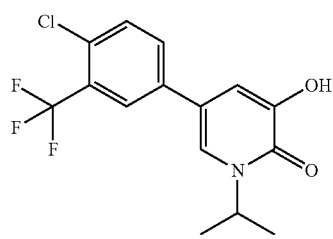

3-(Benzyloxy)-5-bromo-1-(propan-2-yl)pyridin-2(1H)-one

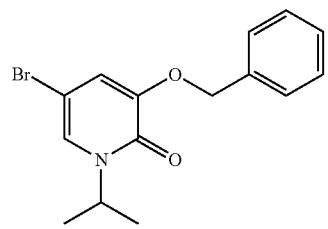 [SMILES: CC(C)n1cc(Br)cc(OCc2ccccc2)c1=O]

3-(Benzyloxy)-5-bromopyridin-2(1H)-one (200 mg, 0.714 mmol), $Cs_2CO_3$ (302 mg, 0.928 mmol), and 2-iodopropane (0.086 mL, 0.857 mmol) were combined in DMF (3 mL) at RT. After stirring overnight the mixture was concentrated. The residue was taken up in $CH_2Cl_2$, filtered through a pad of Celite®, and concentrated. Flash column (Biotage-SNAP-10 g, 0-30% EtOAc/hexanes) gave the title compound as a clear oil (58 mg, 25%) which solidified under vacuum. $^1$H NMR (400 MHz, $CDCl_3$): δ 7.46-7.29 (m, 5 H); 7.05 (d, J=2.4 Hz, 1 H); 6.66 (d, J=2.4 Hz, 1 H); 5.34-5.25 (m, 1 H); 5.09 (s, 2 H); 1.35 (d, J=6.8 Hz, 6 H). LC/MS (M+H)+ 322/324.

5-[4-Chloro-3-(trifluoromethyl)phenyl]-3-hydroxy-1-(propan-2-yl)pyridin-2(1H)-one (2)

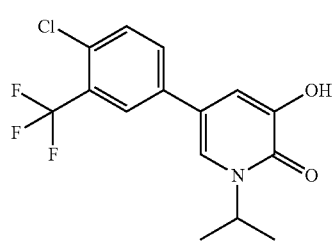

3-(Benzyloxy)-5-bromo-1-(propan-2-yl)pyridin-2(1H)-one (58 mg, 0.180 mmol), 4-chloro-3-(trifluoromethyl)phenylboronic acid (49 mg, 0.218 mmol), and Pd(dppf)Cl$_2$—

CH$_2$Cl$_2$ (8 mg, 9.80 μmol) were combined in THF (1 mL) in a microwave vessel. To this was added 1 M Cs$_2$CO$_3$ (0.540 mL, 0.540 mmol). The vessel was sealed then irradiated to 150° C. for 20 min. The layers were separated and the aqueous extracted with EtOAc (3×). The combined organic layers were filtered through a pad of silica gel washing with EtOAc. The filtrate was concentrated to give 3-(benzyloxy)-5-[4-chloro-3-(trifluoromethyl)phenyl]-1-(propan-2-yl)pyridin-2(1H)-one (86 mg) which was used directly in the next step without purification.

To a solution of crude 3-(benzyloxy)-5-[4-chloro-3-(trifluoromethyl)phenyl]-1-(propan-2-yl)pyridin-2(1H)-one (86 mg) in CH$_2$Cl$_2$ (1 mL) was added ethanethiol (0.075 mL, 1.019 mmol) then BF$_3$—OEt$_2$ (0.13 mL, 1.026 mmol) at RT. After 5 h the mixture was diluted with MeOH and concentrated. The residue was taken up in DMSO:H$_2$O and purified by preparative reversed-phase HPLC (20×150 mm Waters Sunfire (0.1% TFA), 5-70% CH$_3$CN/water over 20 min at 20 mL/min) to give the title compound (24 mg, 36%) as a light tan solid. $^1$H NMR (500 MHz, d$_6$-DMSO): δ 9.28 (s, 1 H); 7.97 (s, 1 H); 7.92 (dd, J=8.4, 2.2 Hz, 1 H); 7.74 (d, J=8.4 Hz, 1 H); 7.68 (d, J=2.4 Hz, 1 H); 7.14 (d, J=2.4 Hz, 1 H); 5.18-5.11 (m, 1 H); 1.39 (d, J=6.8 Hz, 6 H). HRMS (ES) calc (M+H)$^+$=332.0660, found 332.0661.

EXAMPLE 3

5-[4-Chloro-3-(trifluoromethyl)phenyl]-1-(difluoromethyl)-3-hydroxypyridin-2(1H)-one (3)

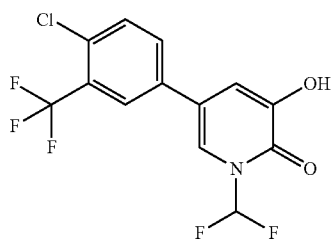

3-(Benzyloxy)-5-bromo-2-chloropyridine

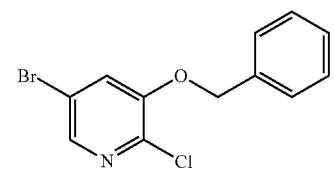 [SMILES: Clc1ncc(Br)cc1OCc1ccccc1]

5-Bromo-2-chloro-pyridin-3-ol (500 mg, 2.399 mmol) and Cs$_2$CO$_3$ (1.2 g, 3.68 mmol) were combined in DMF (10 mL) at RT. To this was added benzyl bromide (0.34 mL, 2.86 mmol). After stirring overnight the mixture was diluted with H$_2$O and extracted with Et$_2$O (3×). The combined organic layers were washed with brine, dried (MgSO$_4$), filtered, and concentrated. Flash column (Biotage-SNAP-50 g, 0-10% EtOAc/hexanes) gave the title compound (674 mg, 94%) as a white solid. $^1$H NMR (500 MHz, CDCl$_3$): δ 8.07 (d, J=2.0 Hz, 1 H); 7.53-7.35 (m, 6 H); 5.16 (s, 2 H). LC/MS (M+H)$^+$ 298/300/302.

3-(Benzyloxy)-5-bromo-1-(difluoromethyl)pyridin-2(1H)-one

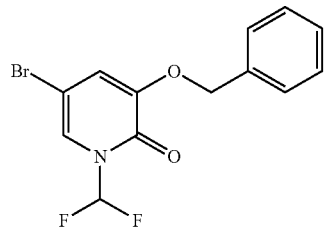 [SMILES: O=c1c(OCc2ccccc2)cc(Br)cn1C(F)F]

3-(Benzyloxy)-5-bromo-2-chloropyridine (100 mg, 0.335 mmol), 2-(fluorosulfonyl)difluoroacetic acid (179 mg, 1.005 mmol), and NaHCO$_3$ (30 mg, 0.357 mmol) were combined in CH$_3$CN (2 mL) then heated to 50° C. After heating overnight the mixture was cooled to RT and diluted with EtOAc. The resulting mixture was filtered through a pad of Celite® and concentrated. Flash column (Biotage-SNAP-10 g, 0-10% EtOAc/hexanes) gave the title compound (38 mg, 34%) as a white solid. $^1$H NMR (500 MHz, CDCl$_3$): δ 7.69 (t, J=60.06 Hz, 1 H); 7.42-7.35 (m, 5 H); 7.22 (d, J=2.2 Hz, 1 H); 6.68 (d, J=2.3 Hz, 1 H); 5.10 (s, 2 H).

5-[4-Chloro-3-(trifluoromethyl)phenyl]-1-(difluoromethyl)-3-hydroxypyridin-2(1H)-one (3)

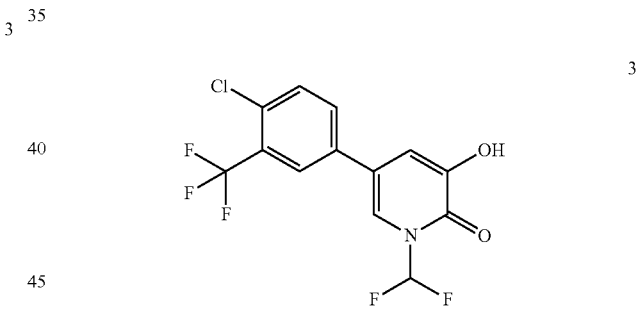

3-(Benzyloxy)-5-bronco-1-(difluoromethyl)pyridin-2(1H)-one (38 mg, 0.115 mmol), 4-chloro-3-(trifluoromethyl)phenylboronic acid (31.0 mg, 0.138 mmol), and Pd(dppf)Cl$_2$—CH$_2$Cl$_2$ (5 mg, 6.12 μmol) were combined in THF (1 mL) in a microwave vessel. To this was added 1 M Cs$_2$CO$_3$ (0.345 mL, 0.345 mmol). The vessel was sealed then irradiated to 150° C. for 20 min. The layers were separated and the aqueous extracted with EtOAc (3×). The combined organic layers were filtered through a pad of silica gel washing with EtOAc. The filtrate was concentrated to give 3-(benzyloxy)-5-[4-chloro-3-(trifluoromethyl)phenyl]-1-(difluoromethyl)pyridin-2(1H)-one (58 mg) which was used directly in the next step without purification.

To a solution of crude 3-(benzyloxy)-5-[4-chloro-3-(trifluoromethyl)phenyl]-1-(difluoromethyl)pyridin-2(1H)-one (58 mg) in CH$_2$Cl$_2$ (1 mL) was added ethanethiol (0.050 mL, 0.675 mmol) then BF$_3$—OEt$_2$ (0.086 mL, 0.675 mmol) at RT. After 3 h the mixture was diluted with MeOH and concentrated. The residue was taken up in DMSO:H$_2$O and purified by preparative reversed-phase HPLC (20×150 mm Waters Sunfire (0.1% TFA), 5-70% CH₃CN/water over 20 min at 20 mL/min) to give the title compound (22 mg, 48%) as an off-white solid. ¹H NMR (500 MHz, d6-DMSO): δ 10.12 (s, 1 H); 8.09-7.90 (m, 3 H); 7.82-7.75 (m, 2 H); 7.25 (d, J=2.3 Hz, 1 H). HRMS (ES) calc (M+H)⁺=340.0158, found 340.0165.

EXAMPLE 4

5-Biphenyl-3-yl-3-hydroxy-1-methylpyridin-2(1H)-one (4)

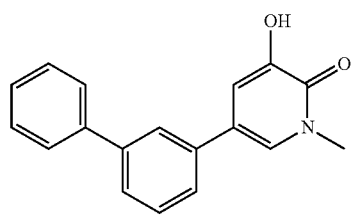

3-(Benzyloxy)-5-(biphenyl-3-yl)-1-methylpyridin-2(1H)-one

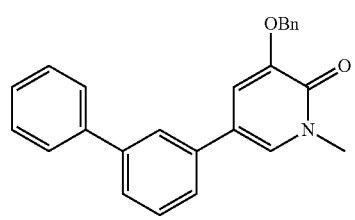 [SMILES: Cn1cc(-c2cccc(-c3ccccc3)c2)cc(OCc2ccccc2)c1=O]

To a mixture of 3-(benzyloxy)-5-bromo-1-methylpyridin-2(1H)-one (38 mg, 0.129 mmol), biphenyl-3-ylboronic acid (31 mg, 0.155 mmol), PdCl₂(dppf).CH₂Cl₂ (5.3 mg, 0.006 mmol), under nitrogen, was added THF (1 mL) followed by 1 M aqueous Na₂CO₃ solution (0.388 mL). The reaction mixture was heated at 150° C. (microwave irradiation) for 25 min, cooled to room temperature and partitioned between water and EtOAc. Layers were separated and the aqueous solution was extracted with CH₂Cl₂ (2×). Combined organic solutions were dried over Na₂SO₄ and concentrated. Purification by flash chromatography (24 g silica gel, 3% to 100% EtOAc in hexanes) afforded 34 mg (72%) of 3-(benzyloxy)-5-(biphenyl-3-yl)-1-methylpyridin-2(1H)-one as a white solid. LC/MS (M+H)⁺ 368.3.

5-Biphenyl-3-yl-3-hydroxy-1-methylpyridin-2(1H)-one (4)

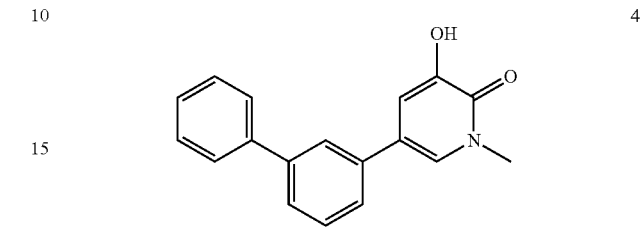

A solution of 3-(benzyloxy)-5-(biphenyl-3-yl)-1-methylpyridin-2(1H)-one (34 mg, 0.093 mmol) in MeOH (5 mL) was hydrogenated under atmospheric H₂ in the presence of 5% Pd/C (15 mg) for 21 h. Filtered and concentrated. Purification by preparative HPLC (5-65% CH₃CN/H₂O over 20 min, 0.05% added TFA) afforded 2.5 mg (10%) of 5-Biphenyl-3-yl-3-hydroxy-1-methylpyridin-2(1H)-one as a white solid. ¹H NMR (500 MHz, CDCl₃): δ 7.63-7.60 (m, 3H), 7.56 (d, J=7.8 Hz, 1H), 7.52-7.43 (m, 3H), 7.41-7.36 (m, 2H), 7.25-7.06 (br, 2H), 3.72 (s, 3H). High resolution mass spec (FT/ICR) calc (M+H)⁺=278.1165 found 278.1176.

EXAMPLE 5

5-(1-benzyl-1H-1,2,3-triazol-4-yl)-3-hydroxy-1-methylpyridin-2(1H)-one (5)

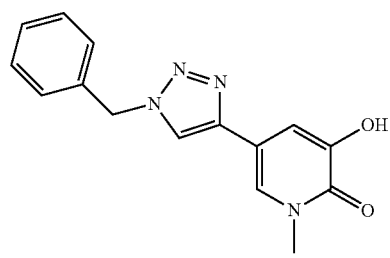

1-methyl-3-{[2-(trimethylsilyl)ethoxy]methoxy}-5-[(trimethylsilyl)ethynyl]pyridin-2(1H)-one

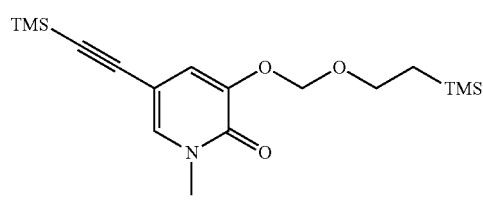 [SMILES: Cn1cc(C#C[Si](C)(C)C)cc(OCOCC[Si](C)(C)C)c1=O]

To a solution of 5-bromo-1-methyl-3-{[2-(trimethylsilyl)ethoxy]methoxy}pyridin-2(1H)-one (2.92 g, 8.74 mmol) in 20 mL THF was added trimethylsilylacetylene (1.72 g, 17.47 mmol), copper (I) iodide (166 mg, 0.874 mmol), diisopropylamine (1.25 mL, 8.74 mmol), and PdCl₂(dppf)-DCM adduct (713 mg, 0.874 mmol). This mixture was microwaved in a sealed vial at 145° C. for 10 minutes. After cooling, the mixture was filtered to remove solids, evaporated, and purified by flash chromatography (50 g silica gel, 0-40% ethyl acetate in hexane) to afford 1-methyl-3-{[2-(trimethylsilyl)ethoxy]methoxy}-5-[(trimethylsilyl)ethynyl]pyridin-2(1H)-one as a dark, viscous oil (2 g, 65% yield). LCMS [M+H]⁺= 352.6

5-ethynyl-1-methyl-3-{[(2-(trimethylsilyl)ethoxy]methoxy}pyridin-2(1H)-one

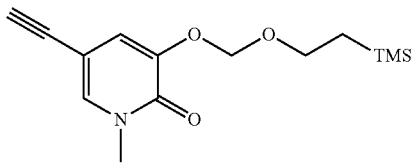 [SMILES: C#Cc1cc(OCOCC[Si](C)(C)C)c(=O)n(C)c1]

To a solution of 1-methyl-3-{[2-(trimethylsilyl)ethoxy]methoxy}-5-[(trimethylsilyl)ethynyl]pyridin-2(1H)-one (2 g, 5.7 mmol) in 35 mL of 1:1 water/methanol was added potassium hydroxide (1.5 g, 26.2 mmol). This mixture was stirred at room temperature for 1 h. Solvent was evaporated under reduced pressure, residue was partitioned between water and ethyl acetate. Aqueous layer was discarded; organic layer dried (Na₂SO₄) and evaporated to afford a dark oil containing 5-ethynyl-1-methyl-3-{[2-(trimethylsilyl)ethoxy]methoxy}pyridin-2(1H)-one, which was used in subsequent steps without further purification. LCMS [M+H]⁺= 280.4.

5-(1-benzyl-1H-1,2,3-triazol-4-yl)-1-methyl-{[2-(trimethylsilyi)ethoxy]methoxy}pyridin-2(1H)-one

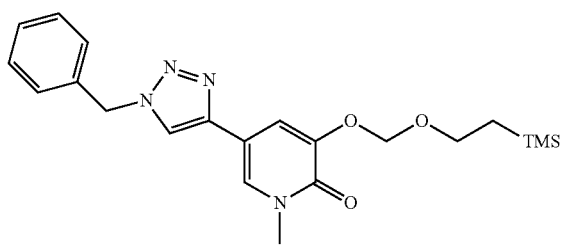 [SMILES: Cn1cc(-c2cn(Cc3ccccc3)nn2)cc(OCOCC[Si](C)(C)C)c1=O]

To a solution of 5-ethynyl-1-methyl-3-{[2-(trimethylsilyl)ethoxy]methoxy}pyridin-2(1H)-one (100 mg, 0.358 mmol) in 2 mL of 50% aqueous tert-butyl alcohol was added (azidomethyl)benzene (47.7 mg, 0.358 mmol), 1-proline (8.24 mg, 0.072 mmol), and copper (I) iodide (13.63 mg, 0.072 mmol). This mixture was microwaved at 145° C. in a sealed vessel for 10 minutes. The mixture was then filtered and evaporated to afford a residue containing 5-(1-benzyl-1H-1, 2,3-triazol-4-yl)-1-methyl-3-{[2-(trimethylsilyl)ethoxy]methoxy}pyridin-2(1H)-one, which was used without further purification. LCMS [M+H]⁺=413.6.

5-(1-benzyl-1H-1,2,3-triazol-4-yl)-3-hydroxy-1-methylpyridin-2(1H)-one (5)

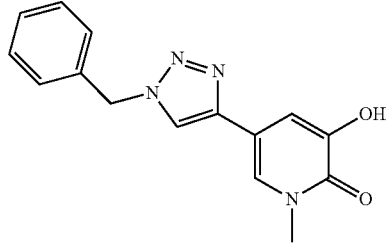

To a solution of containing 5-(1-benzyl-1H-1,2,3-triazol-4-yl)-1-methyl-3-{[2-(trimethylsilyl)ethoxy]methoxy}pyridin-2(1H)-one (148 mg, 0.359 mmol) in 1 mL THF was added 1.1 mL of a 1 M solution of lithium tetrafluoroborate in acetonitrile (1.1 mmol). This mixture was microwaved in a sealed vial at 100° C. for 10 minutes. After cooling, the mixture was evaporated under reduced pressure and purified by reversed-phase HPLC to afford 5-(1-benzyl-1H-1,2,3-triazol-4-yl)-3-hydroxy-1-methylpyridin-2(1H)-one (43.5 mg, 0.154 mmol, 43% yield). ¹H NMR δ (ppm) (DMSO-d₆): 9.28 (1 H, s), 8.38 (1 H, s), 7.75 (1 H, d, J=2.20 Hz), 7.42-7.31 (5 H, m), 5.61 (2 H, s), 3.53 (3 H, s). High resolution mass spec (ESI) calc (M+H)⁺=283.1190 found 283.1188.

EXAMPLE 6

3-Hydroxy-1-methyl-5-(2-oxo-4-phenylpyrrolidin-1-yl)pyridin-2(1H)-one (6)

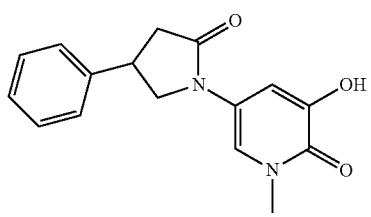

3-(Benzyloxy)-5-bromo-1-methylpyridin-2(1H)-one

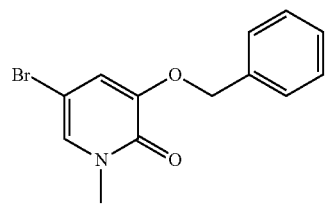 [SMILES: Cn1cc(Br)cc(OCc2ccccc2)c1=O]

To a solution of 3-(benzyloxy)-5-bromopyridin-2(1H)-one (4.4 g, 15.71 mmol) in DMF (50 mL) was added Cs₂CO₃

(6.65 g, 20.42 mmol) then iodomethane (1.2 mL, 19.19 mmol) at RT. After stirring overnight the mixture was concentrated. The residue was taken up in H₂O and extracted with CH₂Cl₂ (3×). The combined organic layers were dried (MgSO₄), filtered, and concentrated. Flash column (Biotage-SNAP-100 g, 50% EtOAc/hexanes) gave the title compound (3.61 g, 78%) as a white solid. $^1$H NMR (500 MHz, CDCl₃): δ 7.43-7.30 (m, 5 H); 7.05 (d, J=2.4 Hz, 1 H); 6.69 (d, J=2.4 Hz, 1 H); 5.24 (s, 0 H); 5.10 (s, 2 H); 3.55 (s, 3 H). LC/MS (M+H)⁺ 294/296.

3-(Benzyloxy)-1-methyl-5-(2-oxo-4-phenylpyrrolidin-1-yl)pyridin-2(1H)-one

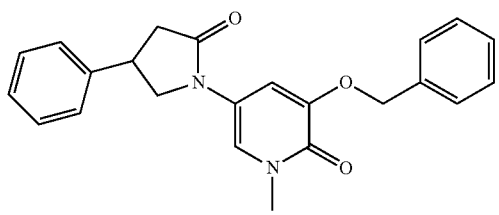 [SMILES: Cn1cc(N2CC(c3ccccc3)CC2=O)cc(OCc2ccccc2)c1=O]

3-(Benzyloxy)-5-bromo-1-methylpyridin-2(1H)-one (100 mg, 0.340 mmol), 4-phenylpyrrolidin-2-one (71 mg, 0.440 mmol), K₃PO₄ (144 mg, 0.680 mmol), CuI (4 mg, 0.021 mmol), and N,N'-dimethylethylenediamine (5 µl, 0.046 mmol) were combined in 1,4-dioxane (1 mL) in a screw cap vial. The vial was sealed then heated to 110° C. After heating overnight the mixture was cooled to RT and diluted with CH₂Cl₂. The resulting mixture was filtered through a pad of Celite®, washing with CH₂Cl₂, and concentrated. Flash column (Biotage-SNAP-25 g, 0-10% MeOH/CH₂Cl₂) gave the title compound (131 mg, 103%) as an off-white foam which was sufficiently pure for use in the next step. $^1$H NMR (500 MHz, CDCl₃): δ 7.44-7.24 (m, 11 H); 7.09 (s, 1 H); 5.15 (s, 2 H); 3.97 (s, 1 H); 3.71-3.65 (m, 2 H); 3.59 (s, 3 H); 3.00-2.92 (m, 1 H); 2.74 (dd, S=16.9, 8.1 Hz, 1 H). LC/MS (M+H)⁺ 375.

3-Hydroxy-1-methyl-5-(2-oxo-4-phenylpyrrolidin-1-yl)pyridin-2(1H)-one (6)

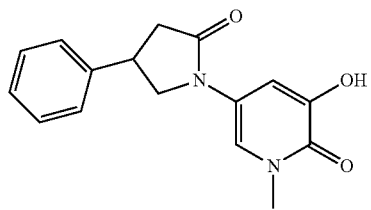

3-(Benzyloxy)-1-methyl-5-(2-oxo-4-phenylpyrrolidin-1-yl)pyridin-2(1H)-one (131 mg, 0.350 mmol) was hydrogenated (balloon) with 10% Pd/C (37 mg, 0.035 mmol) in MeOH (3 mL) at RT. After stirring overnight the mixture was filtered using a 0.45 µm PTFE syringe filter then purified by preparative reversed-phase HPLC (20×150 mm Waters Sunfire (0.1% TFA), 5-50% CH₃CN/water over 20 min at 20 mL/min) to give the title compound (59 mg, 59%) as an off-white solid. $^1$H NMR (500 MHz, CDCl₃): δ 7.52 (d, J=2.6 Hz, 1 H); 7.40-7.28 (m, 5 H); 6.98 (d, J=2.6 Hz, 1 H); 4.08 (t, J=8.4 Hz, 1 H); 3.77-3.66 (m, 2 H); 3.64 (s, 3 H); 2.99 (m, 1 H); 2.76 (m, 1 H). HRMS (ES) calc (M+H)⁺=285.1234, found 285.1228.

EXAMPLE 7

3-Hydroxy-1-methyl-5-(3-phenyl-1H-pyrazol-1-yl)pyridin-2(1H)-one (7)

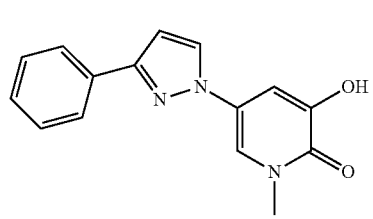

3-(Benzyloxy)-1-methyl-5-(3-phenyl-1H-pyrazol-1-yl)pyridin-2(1H)-one

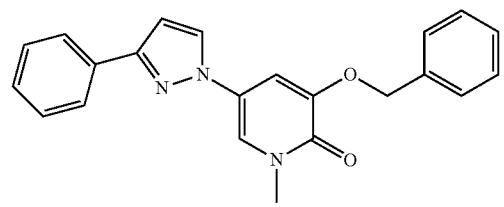 [SMILES: Cn1cc(-n2ccc(-c3ccccc3)n2)cc(OCc2ccccc2)c1=O]

3-(Benzyloxy)-5-bromo-1-methylpyridin-2(1H)-one (50 mg, 0.170 mmol), 3-phenyl-1H-pyrazole (29 mg, 0.201 mmol), K₂CO₃ (47.0 mg, 0.340 mmol), CuI (2 mg, 10.50 µmol), and N,N'-dimethyl-1,2-cyclohexanediamine (6 µl 0.038 mmol) were combined in 1,4-dioxane (0.5 mL) in a screw cap vial. The vial was sealed then heated to 110° C. After stirring overnight the mixture was cooled to RT. CuI (2 mg) and N,N'-dimethyl-1,2-cyclohexanediamine (6 uL) were added and heating continued at 110° C. After stirring overnight the mixture was cooled to RT and diluted with EtOAc. The resulting mixture was filtered and concentrated. The crude material was purified by preparative reversed-phase HPLC (20×150 mm Waters Sunfire (0.1% TFA), 5-70% CH₃CN/water over 20 min at 20 mL/min) to give the title compound (33 mg, 54%) as an amber film. $^1$H NMR (500 MHz, CDCl₃): δ 7.85 (d, J=7.7 Hz, 2 H); 7.61 (d, J=2.5 Hz, 1

H); 7.50-7.32 (m, 9 H); 7.12 (d, J=2.6 Hz, 1 H); 6.73 (d, J=2.5 Hz, 1 H); 5.21 (s, 2 H); 3.68 (s, 3 H). LC/MS (M+H)+ 358.

3-Hydroxy-1-methyl-5-(3-phenyl-1H-pyrazol-1-yl)pyridin-2(1H)-one (7)

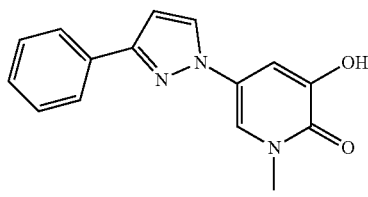

3-(Benzyloxy)-1-methyl-5-(3-phenyl-1H-pyrazol-1-yl)pyridin-2(1H)-one (33 mg, 0.092 mmol) was hydrogenated (balloon) with 10% Pd/C (10 mg, 9.40 µmol) in MeOH (1 mL) at R.T. After stirring overnight the mixture was filtered using a 0.45 µm PTFE syringe filter and concentrated. The crude material was purified by preparative reversed-phase HPLC (20×150 mm Waters Sunfire (0.1% TFA), 5-60% CH₃CN/water over 20 min at 20 mL/ruin) to give the title compound (10 mg, 41%) as an off-white solid. ¹H NMR (500 MHz, CDCl₃): δ 7.86 (d, J=7.6 Hz, 2 H); 7.71 (s, 1 H); 7.49-7.39 (m, 3 H); 7.35 (m, 1 H); 7.21 (s, 1 H); 6.95 (bs, 1 H); 6.75 (d, J=2.4 Hz, 1 H); 3.71 (s, 3 H). HRMS (ES) calc (M+H)+=268.1081, found 268.1071.

EXAMPLE 8

3-Hydroxy-1-methyl-5-(4-phenyl-1H-imidazol-1-yl)pyridin-2(1H)-one (8)

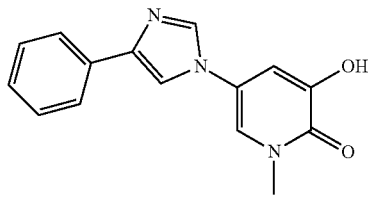

3-(Benzyloxy)-1-methyl-5-(4-phenyl-1H-imidazol-1-yl)pyridin-2(1H)-one

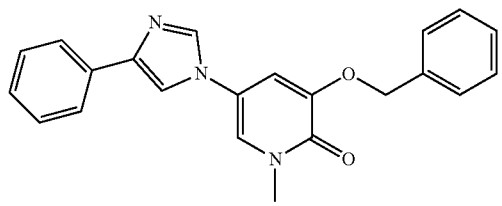 [SMILES: Cn1cc(-n2cnc(-c3ccccc3)c2)cc(OCc2ccccc2)c1=O]

3-(Benzyloxy)-5-bromo-1-methylpyridin-2(1H)-one (50 mg, 0.170 mmol), 4-phenylimidazole (29 mg, 0.201 mmol), Cs₂CO₃ (111 mg, 0.340 mmol), CuI (2 mg, 10.50 µmol), and N,N'-dimethyl-1,2-cyclohexanediamine (6 µl, 0.038 mmol) were combined in DMF (0.5 mL) in a screw cap vial. The vial was sealed then heated to 110° C. After stirring overnight the mixture was cooled to RT. CuI (2 mg) and N,N'-dimethyl-1,2-cyclohexanediamine (6 uL) were added and heating continued at 110° C. After 6 h the mixture was cooled to RT. The mixture was filtered using a 0.45 µm PTFE syringe filter then purified by preparative reversed-phase HPLC (20×150 mm Waters Sunfire (0.1% TFA), 5-50% CH₃CN/water over 20 min at 20 mL/min). Fractions containing the product were pooled then passed through Dowex 1×2-400 ion exchange resin (prewashed with 1M NaOH, H₂O, MeOH) washing with MeOH. The filtrate was concentrated to give the title compound (32 mg, 53%) as an amber film. ¹H NMR (500 MHz, CDCl₃): δ 7.78 (d, J=7.7 Hz, 2 H); 7.59 (s, 1 H); 7.45-7.36 (m, 9 H); 7.13 (d, J=2.5 Hz, 1 H); 6.73 (d, J=2.5 Hz, 1 H); 5.19 (s, 2 H); 3.65 (s, 3 H). LC/MS (M+H)+ 358.

3-Hydroxy-1-methyl-5-(4-phenyl-1H-imidazol-1-yl)pyridin-2(1H)-one (8)

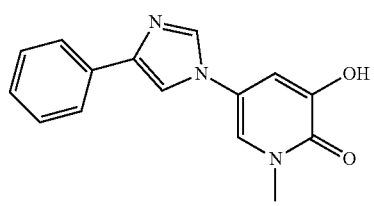

3-(Benzyloxy)-1-methyl-5-(4-phenyl-1H-imidazol-1-yl)pyridin-2(1H)-one (32 mg, 0.090 mmol) was hydrogenated (balloon) with 10% Pd/C (10 mg, 9.40 µmol) in MeOH (1 mL) at RT. After stirring overnight the mixture was filtered using a 0.45 µm PTFE syringe filter and concentrated. The crude material was purified by preparative reversed-phase HPLC (20×150 mm Waters Sunfire (0.1% TFA), 5-40% CH₃CN/water over 20 min at 20 mL/min) to give the TFA salt of the title compound (7.6 mg, 22%) as an off-white solid. ¹H NMR (500 MHz, d6-DMSO): δ 9.82 (bs, 1 H); 8.63 (bs, 1 H); 8.24 (s, 1 H); 7.84-7.79 (m, 3 H); 7.46 (t, J=7.5 Hz, 2 H); 7.33 (m, 1 H); 7.19 (d, J=2.8 Hz, 1 H); 3.56 (s, 3 H). HRMS (ES) calc (M+H)+=268.1081, found 268.1069.

EXAMPLE 9

3-hydroxy-1-methyl-5-(4-phenylpyrimidin-2-yl)pyridin-2(1H)-one (9)

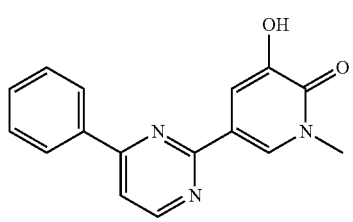

3-(benzyloxy)-5-bromopyridin-2-ol

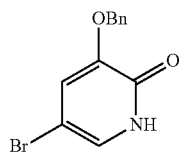

To a solution of 10.68 g (56.2 mmol) 5-bromopyridine-2,3-diol in 290 mL MeOH was added 1(N) aqueous NaOH solution (56.2 mL). A solution of benzyl bromide (5.07 mL, 42.6 mmol) in MeOH (20 mL) was added dropwise to this mixture. After stirring at room temperature for 6 h, the reaction mixture was partitioned between water and EtOAc. Layers were separated and the aqueous phase was extracted with EtOAc (3×). Combined organic solutions were washed with brine (1×), dried over $Na_2SO_4$ and concentrated in vacuo. The resulting solid was recrystallized from MeOH-EtOAc to give 3-(benzyloxy)-5-bromopyridin-2-ol as a white solid (7.9 g, 50%).

3-(benzyloxy)-5-bromo-1-methylpyridin-2(1H)-one

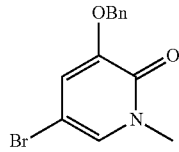 [SMILES: Cn1cc(Br)cc(OCc2ccccc2)c1=O]

To a solution of 3-(benzyloxy)-5-bromopyridin-2-ol ((5.8 g, 20.7 mmol) in DMF (75 mL) was added $Cs_2CO_3$ (8.8 g, 26.9 mmol). A solution of MeI (1.62 mL, 25.9 mmol) in DMF (10 mL) was added dropwise to this mixture. After stirring at room temperature for 3 h, the reaction mixture was concentrated. The residue was taken up in $H_2O$ and the aqueous solution was extracted with $CH_2Cl_2$ (3×). Combined organic solutions washed with brine (1×), dried over $Na_2SO_4$ and concentrated. Purification by flash chromatography (250 g silica gel, 50% EtOAc in hexanes) afforded 4.02 g (66%) of 3-(benzyloxy)-5-bromo-1-methylpyridin-2(1H)-one as a white solid. $^1$H NMR (500 MHz, $CDCl_3$): δ 7.43-7.32 (m, 5H), 7.05 (s, 1H), 6.91 (s, 1H), 5.11 (s, 2H).

[5-(benzyloxy)-1-methyl-6-oxo-1,6-dihydropyridin-3-yl]boronic acid

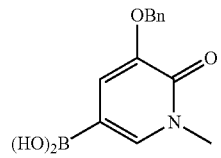

To a solution of isopropylmagnesium chloride (2 M in THF, 2.04 mL) was added LiCl (173 mg, 4.08 mmol) and the resulting solution was stirred for 1 h. THF (3 mL) was added to this solution, cooled to −10° C. Solid 3-(benzyloxy)-5-bromo-1-methylpyridin-2(1H)-one (400 mg, 1.36 mmol) was added and stirred for 1 h. Trimethylborate (0.456 mL, 4.08 mmol) was added to the reaction mixture, stirred at −10° C. for 1 h and then quenched with conc HCl (0.6 mL). The cooling bath was removed, stirred at room temperature overnight and concentrated. Purification by preparative HPLC (5-95% $CH_3CN/H_2O$ over 20 min, 0.05% added TFA) afforded 276 mg [5-(benzyloxy)-1-methyl-6-oxo-1,6-dihydropyridin-3-yl]boronic acid (78%) as a white solid. LC/MS (M+H)$^+$260.2.

3-(benzyloxy)-1-methyl-5-(4-phenylpyrimidin-2-yl)pyridin-2(1H)-one

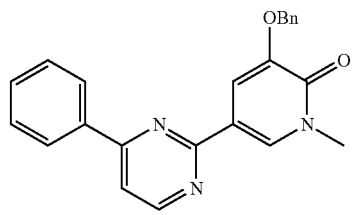 [SMILES: Cn1cc(-c2nccc(-c3ccccc3)n2)cc(OCc2ccccc2)c1=O]

A mixture of [5-(benzyloxy)-1-methyl-6-oxo-1,6-dihydropyridin-3-yl]boronic acid (30 mg, 0.116 mmol), 2-chloro-4-phenylpyrimidine (23.2 mg, 0.122 mmol), bis(tri-t-butylphosphine)palladium(0) (5.9 mg, 0.012 mmol) and potassium fluoride (24 mg, 0.405 mmol) in dioxane (1.5 mL) was stirred at 60° C. for 22 h, cooled to room temperature and filtered through a plug of silica gel (washed with EtOAc). Combined filtrate and washings were concentrated. Purification by preparative HPLC (5-55% $CH_3CN/H_2O$ over 20 min, 0.05% added TFA) afforded 21 mg 3-(benzyloxy)-1-methyl-5-(4-phenylpyrimidin-2-yl)pyridin-2(1H)-one (49%) as a yellow solid. LC/MS (M+H)$^+$ 370.3.

3-hydroxy-1-methyl-5-(4-phenylpyrimidin-2-yl)pyridin-2(1H)-one (9)

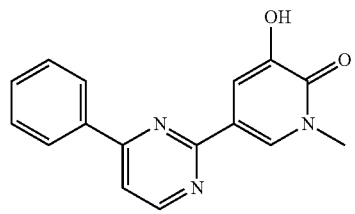

To a solution of 3-(benzyloxy)-1-methyl-5-(4-phenylpyrimidin-2-yl)pyridin-2(1H)-one (21 mg, 0.057 mmol) was added ethanethiol (31.8 mg, 0.512 mmol) followed by $BF_3.OEt_2$ (73 mg, 0.512 mmol). The resulting solution was stirred at room temperature for 18 h, diluted with MeOH and concentrated. Purification by preparative HPLC (5-50% $CH_3CN/H_2O$ over 20 min, 0.05% added TFA) afforded 7.3 mg 3-hydroxy-1-methyl-5-(4-phenylpyrimidin-2-yl)pyridin-2(1H)-one (46%) as a light purple solid. $^1$H NMR (500 MHz, DMSO-$d_6$): δ 9.41 (br s, 1H), 8.84 (d, J=5.3 Hz, 1H); 8.44 (s, 1H); 8.33 (s, 2 H); 7.90 (d, J=5.3 Hz, 1H); 7.72 (s, 1H); 7.59

EXAMPLE 10

2-(biphenyl-3-yl)-5-hydroxy-6-oxo-1,6-dihydropyridine-3-carbonitrile (10)

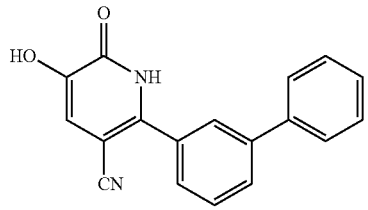

2,3-dibromo-5,6-dimethoxypyridine

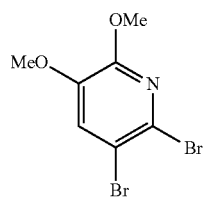 [SMILES: COc1cc(Br)c(Br)nc1OC]

To a solution of 2,3-dimethoxypyridine (10 g, 71.9 mmol) and NaOAc (15.92 g, 194 mmol) in AcOH (140 mL) at 5° C. was added a solution of bromine (10 mL, 194 mmol) in AcOH (40 mL) slowly. The cooling bath was removed, stirred at room temperature for 24 h and then the mixture was poured onto crushed ice followed by neutralization with 25% aqueous NaOH solution. The aqueous phase was extracted with $CH_2Cl_2$ (3×). Combined organic solutions were dried over $Na_2SO_4$ and concentrated. Purification by flash chromatography (80 g silica gel, 1% to 15% EtOAc in hexanes) afforded 5.3 g (25%) of 2,3-dibromo-5,6-dimethoxypyridine as a white solid. LC/MS (M+H)$^+$ 298.0.

2-(biphenyl-3-yl)-3-bromo-5,6-dimethoxypyridine and 3-(biphenyl-3-yl)-2-bromo-5,6-dimethoxypyridine

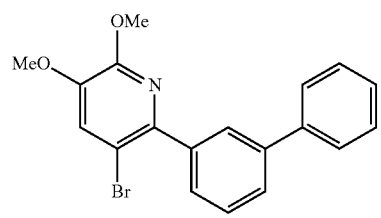

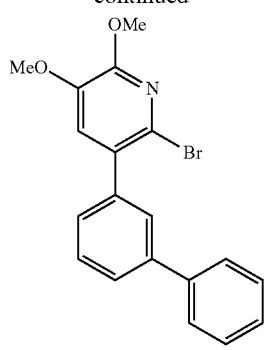

To a mixture of 2,3-dibromo-5,6-dimethoxypyridine (500 mg, 1.684 mmol), 3-biphenylboronic acid (333 mg, 1.684 mmol), Pd(OAc)$_2$ (11.34 mg, 0.051 mmol) and tris(3-sulfonatophenyl)phosphine hydrate sodium salt (97 mg, 0.152 mmol) in DMF (4 mL), under argon, were added diisopropylamine (0.6 mL, 4.21 mmol) and $H_2O$ (1 mL). Stirred at 60° C. for 24 h. Cooled to room temperature and partitioned between water and EtOAc. Layers were separated. Organic phase was washed with water (2×), dried over $Na_2SO_4$ and concentrated. The resulting residue was purified twice, flash chromatography (80 g silica gel, 1% to 10% EtOAc in hexanes) followed by preparative HPLC (15-95% $CH_3CN/H_2O$ over 20 min, 0.05% added $NR_4OH$) to give 222 mg of a mixture of 2-(biphenyl-3-yl)-3-bromo-5,6-dimethoxypyridine and 3-(biphenyl-3-yl)-2-bromo-5,6-dimethoxypyridine (3:1). LC/MS (M+H)$^+$ 372.1.

2-(biphenyl-3-yl)-5,6-dimethoxypyridine-3-carbonitrile

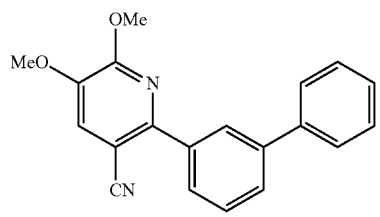 [SMILES: COc1cc(C#N)c(-c2cccc(-c3ccccc3)c2)nc1OC]

To the above mixture of 2-(biphenyl-3-yl)-3-bromo-5,6-dimethoxypyridine and 3-(biphenyl-3-yl)-2-bromo-5,6-dimethoxypyridine (50 mg, 0.135 mmol) were added, under argon, Zn(CN)$_2$ (32 mg, 0.27 mmol), Zn powder (0.9 mg, 0.014 mmol), Pd$_2$(dba)$_3$ (12.4 mg, 0.014 mmol), DPPF (15 mg, 0.027 mmol), DMA (2 mL) and stirred at 120° C. for 3.5 h. Cooled to room temperature and filtered. Purification by preparative HPLC (10->85% $CH_3CN/H_2O$ over 20 min, 0.05% added TFA) afforded 17 mg (39%) of 2-(biphenyl-3-yl)-5,6-dimethoxypyridine-3-carbonitrile as a tan solid. LC/MS (M+H)+ 317.2.

2-(biphenyl-3-yl)-5-hydroxy-6-oxo-1,6-dihydropyridine-3-carbonitrile (10)

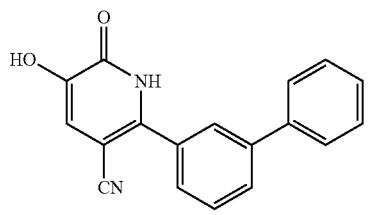

To a solution of 2-(biphenyl-3-yl)-5,6-dimethoxypyridine-3-carbonitrile (17 mg, 0.054 mmol) in CH$_2$Cl$_2$ (1 mL) was added BBr$_3$ solution (1 M in CH$_2$Cl$_2$, 0.537 mL) and stirred at 45° C. for 19 h. The reaction mixture was concentrated and the residue was stirred in 3 N aqueous HCl for 30 min. The precipitated white solid was collected by filtration and purified by preparative HPLC (5-50% CH$_3$CN/H$_2$O over 20 min, 0.05% added TFA) to give 2 mg (13%) of 2-(biphenyl-3-yl)-5-hydroxy-6-oxo-1,6-dihydropyridine-3-carbonitrile as a white solid. $^1$H NMR (500 MHz, CD$_3$OD): δ 7.89 (s, 1H), 7.81 (d, J=7.2 Hz, 1H), 7.70 (d, J=7.6 Hz, 2H), 7.65-7.58 (m, 2H), 7.47 (t, J=7.6 Hz, 2H), 7.38 (t, J=7.4 Hz, 1H) 1 6.96 (s, 1H). High resolution mass spec (FT/ICR) calc (M+H)+ =289.0972 found 289.0969.

EXAMPLE 11

3-(biphenyl-3-yl)-5-hydroxy-6-oxo-1,6-dihydropyridine-2-carbonitrile (11)

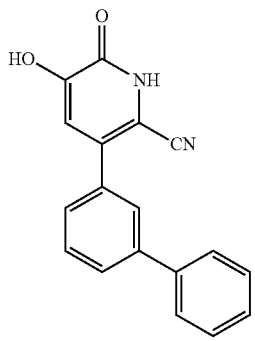

3-Bromo-5,6-dimethoxypyridine-2-carbonitrile

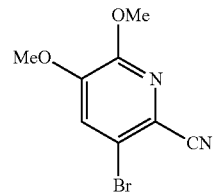

To a mixture of 2,3-dibromo-5,6-dimethoxypyridine (150 mg, 0.505 mmol), Zn(CN)$_2$ (30 mg, 0.253 mmol), Zn powder (33 mg, 0.051 mmol), Pd$_2$(dba)$_3$ (13.9 mg, 0.015 mmol) and DPPF (8.4 mg, 0.015 mmol), under argon, was added DMA (1.5 mL) and stirred at 120° C. for 3.5 h. Cooled to room temperature, filtered and purified by preparative HPLC (10-95% CH$_3$CN/H$_2$O over 20 min, 0.05% added TFA). The desired fractions were loaded onto a Strata-X-C cation exchange column. After washing the column with water and MeOH, the column was eluted with 5% NH$_4$OH in MeOH to give 32 mg (26%) of 3-bromo-5,6-dimethoxypyridine-2-carbonitrile as a tan solid. LC/MS (M+H)+ 243.1.

3-(biphenyl-3-yl)-5,6-dimethoxypyridine-2-carbonitrile

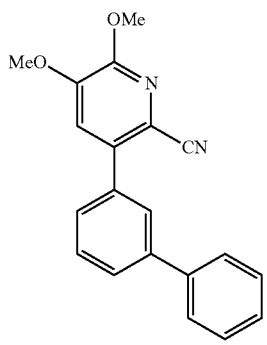 [SMILES: COc1cc(-c2cccc(-c3ccccc3)c2)c(C#N)nc1OC]

To a mixture of 3-bromo-5,6-dimethoxypyridine-2-carbonitrile (31 mg, 0.128 mmol), 3-biphenylboronic acid (30 mg, 0.153 mmol), Pd(OAc)$_2$ (5.7 mg, 0.026 mmol) and tris(3-sulfonatophenyl)phosphine hydrate sodium salt (49 mg, 0.077 mmol) in DMF (1 mL), under argon, were added diisopropylamine (0.045 mL, 0.319 mmol) and H$_2$O (0.25 mL). Stirred at 65° C. for 5 h. Purification by preparative HPLC (10-75% CH$_3$CN/H$_2$O over 20 min, 0.05% added TFA)

afforded 36 mg (89%) of 3-(biphenyl-3-yl)-5,6-dimethoxypyridine-2-carbonitrile as a white solid. LC/MS (M+H)+ 317.1.

3-(Biphenyl-3-yl)-5-hydroxy-6-oxo-1,6-dihydropyridine-2-carbonitrile (11)

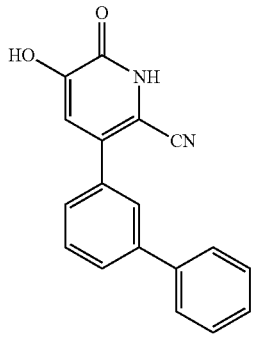

To a solution of 3-(biphenyl-3-yl)-5,6-dimethoxypyridine-2-carbonitrile (34 mg, 0.107 mmol) in CH$_2$Cl$_2$ (1 mL) was added BBr$_3$ solution (1 M in CH$_2$Cl$_2$, 2.149 mL) and stirred at 50° C. for 21 h. The reaction mixture was concentrated and the residue was stirred in 3 N aqueous HCl. After 1 h, this mixture was concentrated and purified by preparative HPLC (5-60% CH$_3$CN/H$_2$O over 20 min, 0.05% added TFA) to give 17 mg (55%) of 3-(biphenyl-3-yl)-5-hydroxy-6-oxo-1,6-dihydropyridine-2-carbonitrile as a light pink solid. $^1$H NMR (400 MHz, CDCl$_3$): δ 7.75-7.65 (m, 2H), 7.65-7.53 (m, 3H), 7.47 (t, J=8.0 Hz, 3H), 7.39 (t, J=7.6 Hz, 1H), 7.12 (s, 1H). LC/MS (M+H)+ 289.2.

EXAMPLE 12

5-Biphenyl-3-yl-4-fluoro-3-hydroxypyridin-2(1H)-one (12)

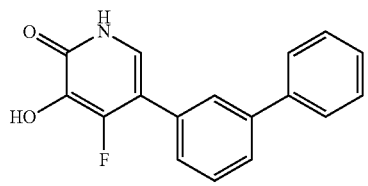

5-(Biphenyl-3-yl)-2,3-dimethoxypyridine

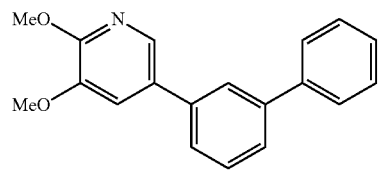 [SMILES: COc1cc(-c2cccc(-c3ccccc3)c2)cnc1OC]

To a mixture of 5-chloro-2,3-dimethoxypyridine (200 mg, 1.15 mmol), biphenyl-3-ylboronic acid (207 mg, 1.045 mmol), PdCl$_2$(dppf).CH$_2$Cl$_2$ (43 mg, 0.052 mmol), under nitrogen, was added. THF (2.5 mL) followed by 1 M aqueous Na$_2$CO$_3$ solution (1.57 mL). The reaction mixture was heated at 150° C. (microwave irradiation) for 40 min, cooled to room temperature and partitioned between water and EtOAc. Layers were separated and the aqueous solution was extracted with EtOAc (2×). Combined organic solutions were dried over Na$_2$SO$_4$ and concentrated. Purification by flash chromatography (24 g silica gel, 1% to 20% EtOAc in hexanes) afforded 104 mg (34%) of 5-(biphenyl-3-yl)-2,3-dimethoxypyridine as a light yellow viscous liquid. LC/MS (M+H)+ 292.2.

5-(Biphenyl-3-yl)-4-fluoro-2,3-dimethoxypyridine

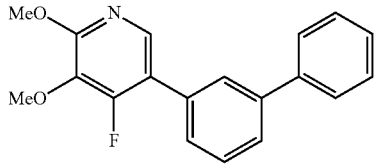 [SMILES: COc1ncc(-c2cccc(-c3ccccc3)c2)c(F)c1OC]

To a solution of 5-(biphenyl-3-yl)-2,3-dimethoxypyridine (52 mg, 0.178 mmol) in THF (2 mL) at −78° C. was added n-BuLi solution in hexane (2.5 M, 0.157 mL) and then the −78° C. bath was replaced with a 0° C. cooling bath. After stirring at this temperature for 50 min, the reaction mixture was cooled down to −78° C. and then solid N-fluorobenzenesulfonimide was added to it. The reaction was quenched after 10 min by adding saturated aqueous NH$_4$Cl solution and then partitioned between EtOAc and saturated aqueous NaHCO$_3$ solution. Layers were separated and the aqueous solution was extracted with EtOAc (2×). Combined organic solutions were dried over Na$_2$SO$_4$ and concentrated. Purification by preparative HPLC (10-85% CH$_3$CN/H$_2$O over 20 min, 0.05% added TFA) afforded 16 mg (29%) of 5-(biphenyl-3-yl)-4-fluoro-2,3-dimethoxypyridine as a colorless viscous material. LC/MS (M+H)+ 310.2.

5-Biphenyl-3-yl-4-fluoro-3-hydroxypyridin-2(1H)-one (12)

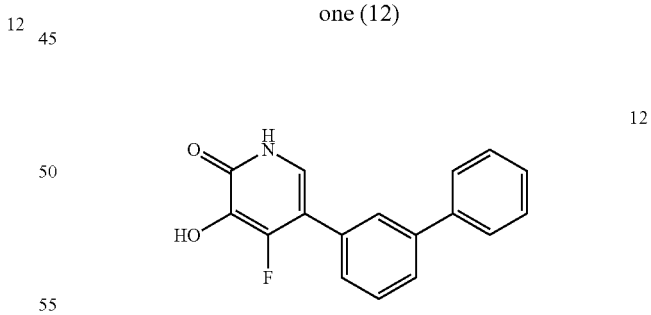

To a solution of 5-(biphenyl-3-yl)-4-fluoro-2,3-dimethoxypyridine (15 mg, 0.048 mmol) in CH$_2$Cl$_2$ (1 mL) was added a methylene chloride solution of BBr$_3$ (1 M, 0.97 mL). After 24 h of stirring at room temperature, the reaction mixture was concentrated and the resulting residue was stirred in 3 N aqueous HCl as a suspension for 1 h. Concentrated, triturated with MeOH and the precipitated solid was collected by filtration, washed with MeOH and dried in vacuo to afford 12 mg (88%) of 5-biphenyl-3-yl-4-fluoro-3-hydroxypyridin-2(1H)-one as a white solid. $^1$H NMR (DMSO-d$_6$, 400 MHz) δ 12.12 (s, 1H), 9.45 (s, 1H), 7.77-7.69 (m, 3H), 7.66-7.64 (m, 1H), 7.54-7.37 (m, 5H), 7.23 (d, J=8.8 Hz, 1H). High resolution mass spec (FT/ICR) calc (M+H)⁺=282.0925 found 282.0921.

EXAMPLE 13

5-Biphenyl-3-yl-4-fluoro-3-hydroxy-1-methylpyridin-2(1H)-one (13)

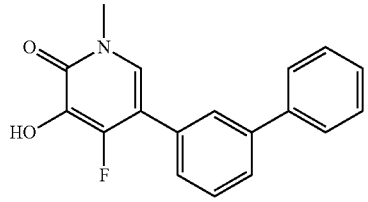

3-(Benzyloxy)-5-(biphenyl-3-yl)-4-fluoropyridin-2(1H)-one

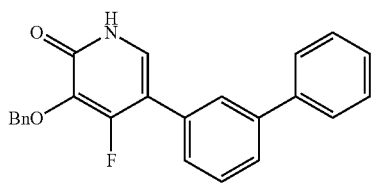 [SMILES: O=c1[nH]cc(-c2cccc(-c3ccccc3)c2)c(F)c1OCc1ccccc1]

To a suspension of 5-biphenyl-3-yl-4-fluoro-3-hydroxypyridin-2(1H)-one (60 mg, 0.213 mmol) was added 1 N aqueous NaOH solution (0.235 mL, 0.235 mmol) and the resulting mixture was sonicated to make a clear solution. To this mixture was added a solution of benzyl bromide (37 mg, 0.213 mmol) in MeOH (0.3 mL) dropwise, stirred overnight at room temperature and then concentrated. Purification by preparative HPLC (10-70% CH₃CN/H₂O over 20 min, 0.05% added TFA) afforded 25 mg (32%) of 3-(benzyloxy)-5-(biphenyl-3-yl)-4-fluoropyridin-2(1H)-one as a white solid. LC/MS (M+H)⁺ 372.2.

3-(Benzyloxy)-5-(biphenyl-3-yl)-4-fluoro-1-methylpyridin-2(1H)-one

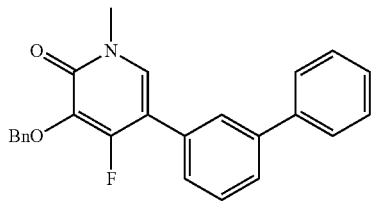 [SMILES: Cn1cc(-c2cccc(-c3ccccc3)c2)c(F)c(OCc2ccccc2)c1=O]

To a solution of 3-(benzyloxy)-5-(biphenyl-3-yl)-4-fluoropyridin-2(1H)-one (24 mg, 0.065 mmol) in DMF (0.8 mL) was added Cs₂CO₃ (27 mg, 0.084 mmol) followed by a solution of MeI (10 mg, 0.071 mmol) in DMF (0.05 mL). After stirring at room temperature for 1 h the reaction mixture was filtered. Purification by preparative HPLC (10-80% CH₃CN/H₂O over 20 min, 0.05% added TFA) afforded 22 mg (88%) of 3-(benzyloxy)-5-(biphenyl-3-yl)-4-fluoro-1-methylpyridin-2(1H)-one as a colorless glass. LC/MS (M−141)⁺ 296.2.

5-Biphenyl-3-yl-4-fluoro-3-hydroxy-1-methylpyridin-2(1H)-one (13)

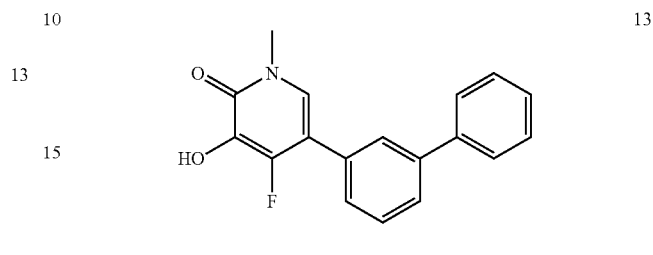

To a solution of 3-(benzyloxy)-5-(biphenyl-3-yl)-4-fluoro-1-methylpyridin-2(1H)-one (22 mg, 0.057 mmol) in CH₂Cl₂ (0.8 mL) was added ethanethiol (53 mg, 0.856 mmol) followed by BF₃.OEt₂ (0.108 mL, 0.856 mmol). The resulting mixture was stirred at room temperature for 3.5 h, diluted with MeOH and concentrated. Purification by preparative HPLC (10-80% CH₃CN/H₂O over 20 min, 0.05% added TFA) afforded 13 mg (77%) of 5-biphenyl-3-yl-4-fluoro-3-hydroxy-1-methylpyridin-2(1H)-one as a white solid. ¹H NMR (500 MHz, CDCl₃): δ 7.61 (d, J=7.9 Hz, 4H), 7.49 (dt, J=22.1, 7.5 Hz, 3H), 7.42-7.35 (m, 2H), 6.99 (d, J=7.9 Hz, 1H), 6.40 (br, 1H), 3.69 (s, 3H). High resolution mass spec (FT/ICR) calc (M+H)⁺=296.1081 found 296.1081.

EXAMPLE 14

5-(Biphenyl-3-yl)-3-hydroxy-6-(1-hydroxy-2-phenylethyl)-1-methylpyridin-2(1H)-one (14)

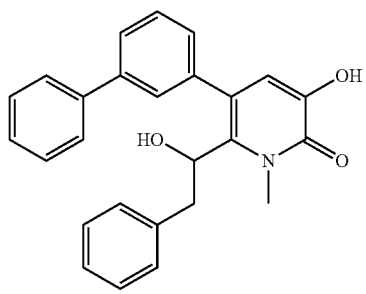

2-Bromo-6-iodopyridin-3-ol

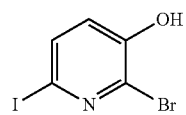

To a suspension of 2-bromopyridin-3-ol (24.1 g, 139 mmol) in 346 mL water was added potassium carbonate (38.3 g, 277 mmol), then iodine (38.7 g, 152 mmol), and this mixture was stirred at room temperature overnight. After cooling to 0° C., 2 N aqueous hydrochloric acid was added until evolution of gas ceased. Acidification was carefully continued until the pH reached ~6, causing a precipitate to form. This precipitate was collected by filtration, washed with water and dried in a vacuum desiccator until reaching constant mass to afford 2-bromo-6-iodopyridin-3-ol (33 g, 79% yield). ES-MS (M+H)⁺=300.

3-(Benzyloxy)-2-bromo-6-iodopyridine

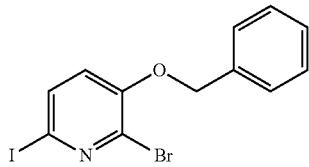 [SMILES: Brc1nc(I)ccc1OCc1ccccc1]

To a solution of 2-bromo-6-iodopyridin-3-ol (10 g, 33.3 mmol) in 100 mL methanol was added potassium carbonate (9.22 g, 66.7 mmol) and benzyl bromide (11.9 mL, 100 mmol), and the resulting mixture was heated to 50° C. overnight under nitrogen. After cooling, the mixture was concentrated under reduced pressure, and the resulting residue was partitioned between water and ethyl acetate. The aqueous layer was removed and discarded. The organic layer was collected, dried over anhydrous magnesium sulfate and concentrated under reduced pressure to afford a residue containing 3-(benzyloxy)-2-bromo-6-iodopyridine. This crude product was used in subsequent steps without further purification. ES-MS (M+H)⁺=391.

3-(Benzyloxy)-6-iodo-2-[(4-methoxybenzyl)oxy] pyridine

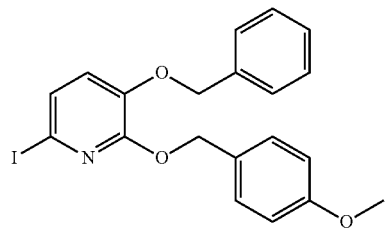 [SMILES: COc1ccc(COc2nc(I)ccc2OCc2ccccc2)cc1]

To a 0° C. solution of p-methoxybenzyl alcohol (13.83 g, 100 mmol) in 33 mL DMF was added sodium hydride (4 g, 100 mmol) slowly. The mixture was stirred at room temperature until evolution of hydrogen had ceased, and crude 3-(benzyloxy)-2-bromo-6-iodopyridine (13.01 g, 33.4 mmol) was added. The resulting solution was heated to 100° C. for 1 h under nitrogen. After cooling, the mixture was diluted with water and extracted with ethyl acetate. The aqueous layer was removed and discarded. The organic layer was collected, dried over anhydrous magnesium sulfate and purified by silica gel chromatography to afford 3-(benzyloxy)-6-iodo-2-[(4-methoxybenzyl)oxy]pyridine (12.1 g, 27.1 mmol, 81% yield). ES-MS (M+H)⁺=448.

3-(Benzyloxy)-6-iodopyridin-2(1H)-one

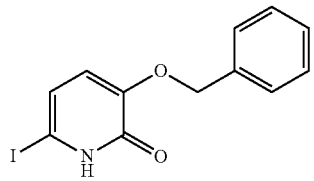 [SMILES: O=c1[nH]c(I)ccc1OCc1ccccc1]

To a solution of 3-(benzyloxy)-6-iodo-2-[(4-methoxybenzyl)oxy]pyridine (28 g, 62.6 mmol) in DCM (63 mL) was added trifluoroacetic acid (4.82 mL, 62.6 mmol). The resulting solution was stirred at room temperature for 30 min. The mixture was concentrated under reduced pressure to afford a bright yellow syrup containing 3-(benzyloxy)-6-iodopyridin-2(1H)-one. This crude product was used in subsequent steps without further purification. ES-MS (M+H)⁺=328.

3-(Benzyloxy)-6-iodo-1-methylpyridin-2(1H)-one

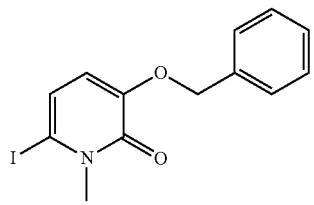 [SMILES: Cn1c(I)ccc(OCc2ccccc2)c1=O]

To a solution of 3-(benzyloxy)-6-iodopyridin-2(1H)-one (20.48 g, 62.6 mmol) in methanol (626 mL) was added potassium carbonate (8.56 g, 62.6 mmol) and iodomethane (3.91 mL, 62.6 mmol), and the resulting mixture was stirred at room temperature for 2 days. The mixture was concentrated under reduced pressure, and the resulting residue was partitioned between water and ethyl acetate. The aqueous layer was removed and discarded. The organic layer was collected, dried over anhydrous magnesium sulfate, and purified using silica gel chromatography to afford 3-(benzyloxy)-6-iodo-1-methylpyridin-2(1H)-one (15.4 g, 45.1 mmol, 72% yield). ES-MS (M+H)⁺=342.

3-(Benzyloxy)-5,6-dibromo-1-methylpyridin-2(1H)-one

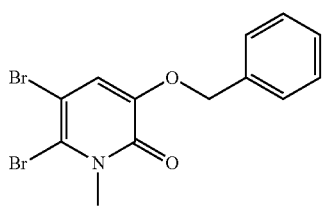 [SMILES: Cn1c(Br)c(Br)cc(OCc2ccccc2)c1=O]

To a solution of 3-(benzyloxy)-6-iodo-1-methylpyridin-2(1H)-one (15.4 g, 45.1 mmol) in 451 mL acetic acid was added bromine (9.3 mL, 181 mmol). The resulting solution was allowed to stir at room temperature overnight. The solid material formed was collected by filtration, washed with a small amount of acetic acid, and dried under reduced pressure to afford 3-(benzyloxy)-5,6-dibromo-1-methylpyridin-2 (1H)-one (10.3 g, 27.6 mmol, 61.2% yield). ES-MS (M+H)$^+$=374.

5-(Benzyloxy)-3-bromo-1-methyl-6-oxo-1,6-dihydropyridine-2-carbaldehyde

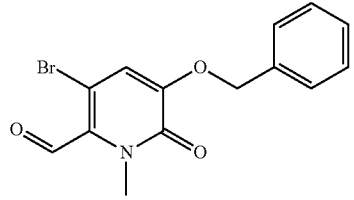 [SMILES: Cn1c(C=O)c(Br)cc(OCc2ccccc2)c1=O]

To a −78° C. solution of 3-(benzyloxy)-5,6-dibromo-1-methylpyridin-2(1H)-one (1.5 g, 4.02 mmol) in THF (20 mL) was added 2 M isopropylmagnesium chloride in THF (4.02 mL, 8.04 mmol) dropwise. This mixture was stirred at −78° C. for 15 minutes under nitrogen, and N-methyl-N-pyridin-2-ylformamide (1.4 mL, 12.06 mmol) was added. The mixture was allowed to slowly warm to room temperature overnight. Volatiles were removed under reduced pressure, and the resulting residue was partitioned between dilute aqueous hydrochloric acid and ethyl acetate. The aqueous layer was removed and discarded. The organic layer was collected, dried over anhydrous magnesium sulfate, and purified by silica gel chromatography to afford 5-(benzyloxy)-3-bromo-1-methyl-6-oxo-1,6-dihydropyridine-2-carbaldehyde (1.09 g, 3.38 mmol, 84% yield). ES-MS (M+H)$^+$=323.

3-(Benzyloxy)-5-bromo-6-(1-hydroxy-2-phenylethyl)-1-methylpyridin-2(1H)-one

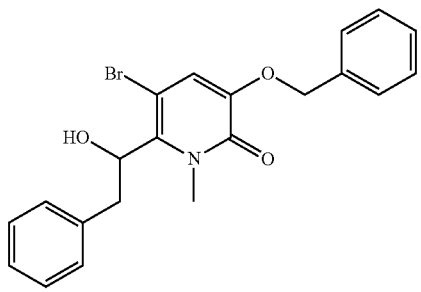 [SMILES: Cn1c(C(O)Cc2ccccc2)c(Br)cc(OCc2ccccc2)c1=O]

To a 0° C. solution of 5-(benzyloxy)-3-bromo-1-methyl-6-oxo-1,6-dihydropyridine-2-carbaldehyde (1.09 g, 3.38 mmol) in 34 mL THF was added benzylmagnesium chloride (2.55 g, 3.38 mmol) dropwise. The mixture was allowed to stir at 0° C. for 1 h. After warming to room temperature, volatiles were removed under reduced pressure. The resulting residue was partitioned between dilute aqueous hydrochloric acid and ethyl acetate. The aqueous layer was removed and discarded, and the organic layer was collected, dried over anhydrous magnesium sulfate and purified by silica gel chromatography to afford 3-(benzyloxy)-5-bromo-6-(1-hydroxy-2-phenylethyl)-1-methylpyridin-2(1H)-one (1 g, 2.41 mmol, 71% yield). ES-MS (M+H)$^+$=415.

3-(Benzyloxy)-5-(biphenyl-3-yl)-6-(1-hydroxy-2-phenylethyl)-1-methylpyridin-2(1H)-one

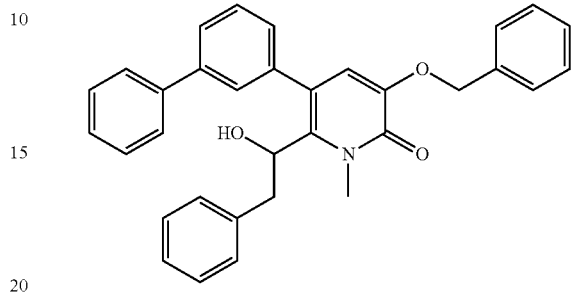

To a solution of 3-(benzyloxy)-5-bromo-6-(1-hydroxy-2-phenylethyl)-1-methylpyridin-2(1H)-one (0.34 g, 0.821 mmol) in 2 mL THY was added PdCl$_2$(dppf)-CH$_2$Cl$_2$ adduct (67 mg, 0.082 mmol), biphenyl-3-ylboronic acid (179 mg, 0.903 mmol), and 1 N aqueous cesium carbonate solution (2 mL, 2 mmol). The resulting mixture was microwaved in a sealed vial at 155° C. for 10 min. The aqueous layer was removed and discarded, and the organic layer was collected, dried over anhydrous magnesium sulfate, concentrated and purified by silica gel chromatography to afford 3-(benzyloxy)-5-(biphenyl-3-yl)-6-(1-hydroxy-2-phenylethyl)-1-methylpyridin-2(1H)-one (100 mg, 0.205 mmol, 25% yield).

5-(Biphenyl-3-yl)-3-hydroxy-6-(1-hydroxy-2-phenylethyl)-1-methylpyridin-2(1H)-one (14)

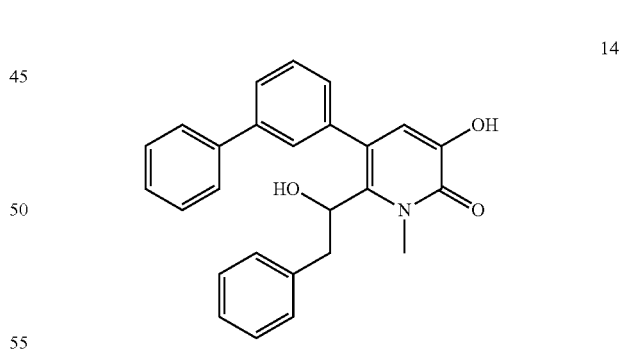

14

To a solution of 3-(benzyloxy)-5-(biphenyl-3-yl)-6-(1-hydroxy-2-phenylethyl)-1-methylpyridin-2(1H)-one (100 mg, 0.205 mmol) in 5 mL methanol, was added 10% palladium on charcoal (21.83 mg, 0.02 mmol). The resulting mixture was stirred at room temperature under hydrogen (1 atm) for 45 min. The mixture was filtered to remove charcoal, concentrated and purified by reversed-phase HPLC to afford 5-(biphenyl-3-yl)-3-hydroxy-6-(1-hydroxy-2-phenylethyl)-1-methylpyridin-2(1H)-one (25.4 mg, 0.064 mmol, 31.2%

EXAMPLE 15

6-(1-Benzyl-1H-pyrazol-4-yl)-3-hydroxy-1H-pyridin-2-one (15)

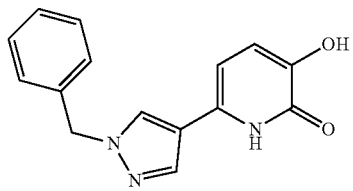

To a suspension of 0.05 g (0.17 mmol) 1-benzyl-4-(4,4,5,5-tetramethyl-[1,3,2]dioxaborolan-2-yl)-1H-pyrazole in 1 mL (1 mmol) 1 M aq. $Cs_2CO_3$, was added 1 mL of a THF solution containing 2.7 mg (0.005 mmol) bis(tri-tert-butylphosphine)palladium and 0.035 g (0.11 mmol) 3-benzyloxy-6-iodo-1H-pyridin-2-one. The resulting mixture was heated by microwave to 150° C. for 10 min. After cooling, the aqueous layer was removed by pipette, and the remaining organics were concentrated. The resulting residue was dissolved in 2 mL EtOH/AcOH (10:1), 0.05 g (0.047 mmol) Pd/C (10%) was added, and the resulting suspension was placed under a hydrogen atmosphere (1 atm) with stirring for 6 h. The mixture was then filtered through Celite and concentrated. Purification by automated mass-guided HPLC afforded 1.7 mg (4.2%) 3-hydroxy-6-(4-phenoxy-phenyl)-1H-pyridin-2-one. $^1$H NMR δ (ppm) (DMSO-$d_6$): 8.29 (1 H, s), 7.95 (1 H, s), 7.39-7.23 (7 H, m), 6.71 (1 H, d, J=7.46 Hz), 6.32 (1 H, d, 7.41 Hz), 5.32 (2 H, s). High resolution mass spec (FT/ICR) calc (M+H)$^+$=268.1081 found 268.1078.

EXAMPLE 16

6-(4-Chlorophenyl)-3-hydroxy-1-methylpyridin-2(1H)-one (16)

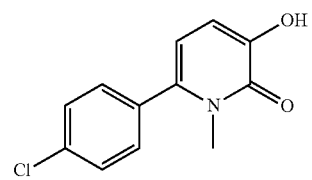

6-(4-chlorophenyl)-3-methoxy-1-methylpyridin-2(1H)-one

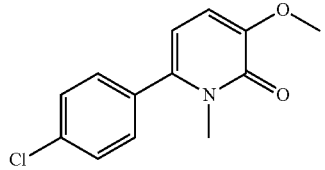 [SMILES: COc1ccc(-c2ccc(Cl)cc2)n(C)c1=O]

To a solution of 6-iodo-3-methoxy-1-methylpyridin-2 (1H)-one (100 mg, 0.377 mmol) in 2 mL THF was added 4-chlorophenylboronic acid (59 mg, 0.377 mmol), $PdCl_2$(dppf)-DCM adduct (30.8 mg, 0.038 mmol) and 1 M aqueous cesium carbonate (1 mL, 1 mmol) heated in a sealed vial to 160° C. for 10 minutes. After cooling, the aqueous layer was removed and discarded. The organic layer was collected, dried and evaporated to afford a residue containing 6-(4-chlorophenyl)-3-methoxy-1-methylpyridin-2(1H)-one. This crude residue was used in subsequent steps without further purification.

6-(4-chlorophenyl)-3-hydroxy-1-methylpyridin-2(1H)-one (16)

To a solution of crude 6-(4-chlorophenyl)-3-methoxy-1-methylpyridin-2(1H)-one in 5 mL acetonitrile was added iodotrimethylsilane (154 µL, 1.132 mmol) and the mixture was heated to 150° C. for 10 minutes. The reaction mixture was quenched with excess methanol, evaporated and purified using reversed-phase HPLC to afford 6-(4-chlorophenyl)-3-hydroxy-1-methylpyridin-2(1H)-one (17.3 mg, 19.44% yield). $^1$H NMR (499 MHz, DMSO-$d_6$): δ 7.68 (d, 1 H), 7.49 (dd, 1 H), 3.74 (s, 1 H), 2.54 (s, 1 H).

High resolution mass spec (ESI) calc (M+H)$^+$=236.0473 found 236.0471

Assays

The activity of the compounds in accordance with the present invention as COMT inhibitors may be readily determined without undue experimentation using a fluorescence or fluorescence polarization (FP) methodology that is well known in the art (Kurkela M et al., Anal Biochem (331) 2004, 198-200 and Graves, T L et al., Anal Biochem (373) 2008, 296-306). Assays utilized purified human COMT enzyme of the Val158 variant (membrane-bound MB-COMT or soluble S—COMT) containing a C-terminal 6 or 10-histidine tag. Compounds of the following examples had activity in reference assays by exhibiting the ability to inhibit the methylation of esculetin and/or inhibit the production of S-adenosyl-homocysteine (SAH). Any compound exhibiting an $IC_{50}$ below 1 µM would be considered a COMT inhibitor as defined herein.

In a typical experiment the COMT inhibitory activity of the compounds of the present invention was determined in accordance with the following experimental methods detailed below. The fluorescence assay was based on methylation of a substrate (6,7-dihydroxycoumarin or 'esculetin') by COMT to produce a highly fluorescent product (7-hydroxy-6-methoxycoumarin or scopoletin'). The reaction requires the presence of magnesium ions and a methyl donor, in this case 5-adenosylmethionine (SAM). A 10 mM compound stock in DMSO was used to prepare 10 point 3-fold dilution series and 1 uL of appropriate dilution was plated into assay wells (black 96 well round bottom polystyrene plates from Costar; catalog #3792). Recombinant enzyme was diluted in assay buffer (100 mM $Na_2HPO_4$ pH 7.4, 1 mM DTT, 0.005% Tween-20) and 35 µL was added to assay wells containing 1 µL of compound. Preincubation of COMT enzyme and compound proceeded for 2 hours at room temperature. Enzyme assays were initiated with 5 uL of a mixture containing 40 µM SAM (USB catalog #US10601), 4 µM esculetin (substrate) and 40 mM $MgCl_2$. The formation of product (scopoletin) was monitored over time by fluorescence (excitation 340 nm, emission 460 nm, no lag, 100 µs integration time, 5 flashes, top read) using a Tecan Safire² plate reader. Assays were monitored over time until a signal to background of 4 to 1 was achieved. Titration curves and $IC_{50}$ values were calculated using standard procedures. Briefly, data were calculated as (mean of test wells)−(mean of no-enzyme controls)/(mean of total enzyme controls)−(mean of no-enzyme controls), then expressed as a percentage and subtracted from 100 to give percent inhibition of COMT activity. In some cases, compounds were not preincubated with MB-COMT for 2 hours at room temperature prior to starting the enzyme assays.

To determine $IC_{50}$ values in the fluorescence polarization assay, solutions of test compounds were prepared and preincubated with COMT enzyme as stated above. Enzyme reactions were initiated upon the addition of 5 µL of an 8× mix prepared in assay buffer containing 8 µM SAM (USB catalog #US10601), 16 µM dopamine (Sigma catalog #H8502) and 40 mM $MgCl_2$. After 25 minutes incubation at room temperature, reactions were quenched with 5 µL 250 mM EDTA, pH 8.2. To quenched reactions, 20 µL of a preformed complex containing S-adenosyl-L-cysteine (SAC) TAMRA tracer (2 mM from Anaspec diluted 1:80,000) and a 1:20 dilution of anti-S-adenosyl-L-homocysteine antibody (mouse monoclonal from Abbott Homocysteine detection kit, catalog #7D29-20) was prepared in assay buffer II ($Na_2HPO_4$ pH 7.2). Prior to combining with quenched enzyme assays, the SAH antibody/SAC TAMRA tracer complex was preformed at room temperature for 30 minutes while protected from light. Therefore, the final concentration of the SAH antibody/SAC TAMRA mix was 1:60 and 1:240,000, respectively. After a 2.5 hour incubation at room temperature, protected from light, fluorescence polarization was measured using a Tecan Safire² plate reader (excitation 530 nm, emission 595 nm). Titration curves and $IC_{50}$ values were calculated using standard protocols.

The compounds of formula I have an $IC_{50}$ activity of 100 µM or less for COMT. Many of the compounds of formula I have an IC50 of less than 200 nM. For example, the compounds below have $IC_{50}$<400 nM in the "Esculetin or Fluorescence Polarization assay". In particular, the compounds of Examples 1 and 4 on pages 34-36 and Compounds 1, 2, and 8 in Table 1 exhibited the following $IC_{50}$ (nM) values:

| Compound | MB-COMT IC50-(nM) |
|---|---|
| Example 1 | 392 |
| Example 4 | 118 |
| Compound #1 | 179 |
| Compound #2 | 31 |
| Compound #8 | 197 |

What is claimed:
1. A compound of structural formula I:

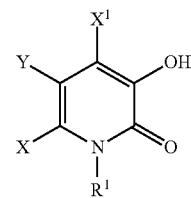

including tautomers or pharmaceutically acceptable salts and individual enantiomers and diastereomers thereof wherein:

Y represents $C_{2-6}$ alkynyl, $CH_2C_{5-10}$ heterocyclyl, $(CH_2)_2 C_{5-10}$ heterocyclyl, $(CH_2)_3 C_{5-10}$ heterocyclyl, $(CH_2)_4 C_{5-10}$ heterocyclyl, $(CH_2)_5 C_{5-10}$ heterocyclyl, $(CH_2)_n C_{6-10}$ aryl, said alkynyl, heterocyclyl and aryl substituted with 1 to 3 groups of $R^a$;

$X^1$, and $R^1$ independently represent hydrogen, halo, CN, $C_{1-6}$ alkyl, $C_{2-6}$ alkynyl, $(CH_2)_n C_{6-10}$ aryl, $(CH_2)_n C_{5-10}$ heterocyclyl, said alkyl, heterocyclyl, and aryl optionally substituted with 1 to 3 groups of $R^a$;

X represents hydrogen, halo, CN, $C_{1-6}$ alkyl, $C_{2-6}$ alkynyl, $(CH_2)_n C_{6-10}$ aryl, said alkyl and aryl optionally substituted with 1 to 3 groups of $R^a$;

$R^2$ represents H, OH, $C_{1-6}$ alkyl, $N(CH_3)_2$, $(CH_2)_n C_{3-10}$ cycloalkyl, $(CH_2)_n C_{5-10}$ heterocyclyl, $(CH_2)_n C_{6-10}$ aryl, said aryl and heterocyclyl optionally substituted with 1 to 3 groups of $R^a$;

$R^a$ represents $C_{1-6}$ alkyl, halogen, hydroxyl, $C_{2-4}$alkynyl, $(CH_2)_n CF_3$, $OCHF_2$, $OCF_3$, $C_{3-6}$ cycloalkyl, $NR^2C(O)R^2$, $C(O)N(R^2)_2$, $C(R^2)_2OR^2$, $C(O)R^2$, $NO_2$, CN, $N(R^2)_2$, $(CH_2)_n C(O)OR^2$, $SO_2R^2$, $NHSO_2R^2$, $OR^2$, $(CH_2)_n C_{5-10}$ heterocyclyl, $C(O)(CH_2)_n C_{5-10}$ heterocyclyl, $(CH_2)_n C_{6-10}$ aryl, or $C(O)(CH_2)_n C_{6-10}$ aryl, said alkyl, alkynyl, cycloalkyl, heterocyclyl and aryl optionally substituted with 1 to 3 groups of $R^b$;

$R^b$ represents $C_{1-6}$ alkyl, halogen, $CHF_2$, $OCHF_2$, —O—, $N(R^2)_2$, $CH_2OH$, $(CH_2)_n C_{6-10}$ aryl, $(CH_2)_n C_{5-10}$ heterocyclyl, $OR^2$, $C_{3-6}$cycloalkyl, $(CH_2)_n CF_3$, or CN; and n represents 0 to 5.

2. The compound according to claim 1 wherein Y is $(CH_2)_n C_{6-10}$ aryl selected from the group consisting of phenyl and naphthyl, said phenyl and naphthyl substituted with 1 to 3 groups of $R^a$.

3. The compound according to claim 1 wherein Y is $(CH_2)_2 C_{5-10}$ heterocyclyl, $(CH_2)_2 C_{5-10}$ heterocyclyl, $(CH_2)_3 C_{5-10}$ heterocyclyl, $(CH_2)_4 C_{5-10}$ heterocyclyl, $(CH_2)_5 C_{5-10}$ heterocyclyl, said heterocyclyl selected from the group consisting of quinolinyl, isoquinolinyl, thiazolyl, triazolyl, pyrrolyl, pyrrolidinyl, pyrazolyl, imidazolyl, and pyrimidinyl all of which are substituted with 1 to 3 groups of $R^a$.

4. The compound according to claim 1, wherein Y is $C_{2-6}$ alkynyl substituted with 1 to 3 groups of $R^a$.

5. The compound according to claim 1, wherein $R^1$ is optionally substituted $C_{1-6}$ alkyl or hydrogen and X and $X^1$ both are hydrogen.

6. The compound according to claim 1 wherein the $R^a$ substituent on Y is selected from the group consisting of $C_{1-6}$alkyl, $CF_3$, $OCF_3$, halo, CN, $NHSO_2R^2$, —$NHC(O)R^2$, $C(O)N(R^2)2$, $(CH_2)_nC_{6-10}$ aryl, $C(O)(CH_2)_nC_{6-10}$ aryl, $C_{5-10}$ heterocyclyl, $C(O)C_{5-10}$ heterocyclyl, $OC_{1-6}$alkyl, and $OC_{6-10}$aryl, said alkyl, aryl and heterocyclyl optionally substituted with 1 to 3 groups of $R^b$.

7. The compound according to claim 1 represented by structural formula Ia:

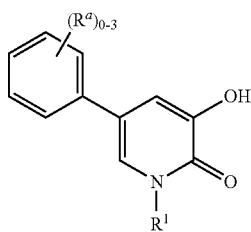

Ia including tautomer or pharmaceutically acceptable salts and individual enantiomers and diastereomers thereof wherein $R^1$ is hydrogen or $C_{1-6}$ alkyl, and $R^a$ is selected from the group consisting of $C_{1-6}$alkyl, $CF_3$, $OCF_3$, halo, CN, $NHSO_2R^2$, $NHC(O)R^2$, $C(O)N(R^2)2$, $(CH_2)_nC_{6-10}$ aryl, $C(O)(CH_2)_nC_{6-10}$ aryl, $C_{5-10}$ heterocyclyl, $C(O)C_{5-10}$ heterocyclyl, $OC_{1-6}$alkyl, and $OC_{6-10}$aryl, said alkyl, aryl and heterocyclyl optionally substituted with 1 to 3 groups of $R^b$.

8. The compound according to claim 1 represented by structural formula Ib:

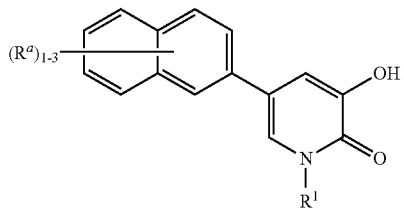

Ib including tautomer or pharmaceutically acceptable salts and individual enantiomers and diastereomers thereof wherein $R^1$ is hydrogen or $C_{1-6}$ alkyl, and $R^a$ is selected from the group consisting of $C_{1-6}$alkyl, $CF_3$, $OCF_3$, halo, CN, $NHSO_2R^2$, $NHC(O)R^2$, $C(O)N(R^2)2$, $(CH_2)_nC_{6-10}$ aryl, $C(O)(CH_2)_nC_{6-10}$ aryl, $C_{5-10}$ heterocyclyl, $C(O)C_{5-10}$ heterocyclyl, $OC_{1-6}$alkyl, and $OC_{6-10}$aryl, said alkyl, aryl and heterocyclyl optionally substituted with 1 to 3 groups of $R^b$.

9. The compound according to claim 1 represented by structural formula Ic:

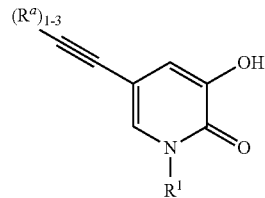

Ic including tautomer or pharmaceutically acceptable salts and individual enantiomers and diastereomers thereof wherein $R^1$ is hydrogen or $C_{1-6}$ akyl, and $R^a$ is selected from the group consisting of $C_{1-6}$ alkyl, $CF_3$, $OCF_3$, halo, CN, $NHSO_2R^2$, $NHC(O)R^2$, $C(O)N(R^2)_2$, $(CH_2)_n C_{6-10}$ aryl, $C(O)(CH_2)_nC_{6-10}$ aryl, $C_{5-10}$ heterocyclyl, $C(O)C_{5-10}$ heterocyclyl, $OC_{1-6}$alkyl, and $OC_{6-10}$aryl, said alkyl, aryl and heterocyclyl optionally substituted with 1 to 3 groups of $R^b$.

10. A compound which is:
3-hydroxy-1-methyl-5-naphthalen-2-ylpyridin-2(1H)-one;
5-[4-chloro-3-(trifluoromethyl)phenyl]-3-hydroxypyridin-2(1H)-one;
3-hydroxy-5-(isoquinolin-4-yl)pyridin-2(1H)-one;
3-hydroxy-5-[4-(morpholin-4-ylcarbonyl)phenyl]pyridin-2(1H)-one;
3-hydroxy-1-methyl-5-[4-(trifluoromethoxy)phenyl]pyridin-2(1H)-one;
3-hydroxy-1-methyl-5-[4-(2-methylpropyl)phenyl]pyridin-2(1H)-one;
3-hydroxy-5-(naphthalen-1-yl)pyridin-2(1H)-one;
3-(5-hydroxy-6-oxo- 1,6-dihydropyridin-3-yl)benzonitrile;
3-hydroxy-5-[3-(trifluoromethoxy)phenyl]pyridin-2(1H)-one;
N-[3-(5-hydroxy-6-oxo-1,6-dihydropyridin-3-yl)phenyl]-4-methylbenzenesulfonamide;
N-[5-(5-hydroxy-6-oxo-1,6-dihydropyridin-3-yl)-1,3-thiazol-2-yl]acetamide;
5-[4-chloro-3-(trifluoromethyl)phenyl]-1-ethyl-3-hydroxypyridin-2(1H)-one;
5-[4-chloro-3-(trifluoromethyl)phenyl]-3-hydroxy-1-(2,2,2-trifluoroethyl)pyridin-2(1H)-one;
3-hydroxy-1-methyl-5-[3-(3-methyl-1,2,4-oxadiazol-5-yl)phenyl]pyridin-2(1H)-one;
N-cyclohexyl-4-(5-hydroxy-1-methyl-6-oxo-1,6-dihydropyridin-3-yl)-N-methylbenzamide;
5-[(2,4-dichlorophenyl)ethynyl]-3-hydroxy-1-methylpyridin-2(1H)-one;
5-biphenyl-3-yl-6-bromo-3-hydroxypyridin-2(1H)-one;
3-hydroxy-1-methyl-6-(phenylethynyl)pyridin-2(1H)-one;
6-biphenyl-4-yl-3-hydroxy-1-methylpyridin-2(1H)-one;
3-hydroxy-1-methyl-6-[4-(phenylcarbonyl)phenyl]pyridin-2(1H)-one;
5-[4-(2,3-dihydro-1,4-benzoxazepin-4(5H)-ylcarbonyl)phenyl]-3-hydroxy-1-methylpyridin-2(1H)-one;
5-[4-chloro-3-(trifluoromethyl)phenyl]-3-hydroxy-1-methylpyridin-2(1H)-one;
6-(3,4-dichlorophenyl)-3-hydroxy-1-methylpyridin-2(1H)-one;
5-(2,4-Dichloro-phenyl)-3-hydroxy-1-methyl-1H-pyridin-2-one;
5-[4-Chloro-3-(trifluoromethyl)phenyl]-3-hydroxy-1-(propan-2-yl)pyridin-2(1H)-one;

5-[4-Chloro-3-(trifluoromethyl)phenyl]-1-(difluoromethyl)-3-hydroxypyridin-2(1H)-one;
5-Biphenyl-3-yl-3-hydroxy-1-methylpyridin-2(1H)-one;
5-(1-benzyl-1H-1,2,3-triazol-4-yl)-3-hydroxy-1-methylpyridin-2(1H)-one;
3-Hydroxy-1-methyl-5-(2-oxo-4-phenylpyrrolidin-1-yl)pyridin-2(1H)-one;
3-Hydroxy-1-methyl-5-(3-phenyl-1H-pyrazol-1-yl)pyridin-2(1H)-one;
3-Hydroxy-1-methyl-5-(4-phenyl-1H-imidazol-1-yl)pyridin-2(1H)-one;
3-hydroxy-1-methyl-5-(4-phenylpyrimidin-2-yl)pyridin-2(1H)-one;
2-(biphenyl-3-yl)-5-hydroxy-6-oxo-1,6-dihydropyridine-3-carbonitrile;
3-(biphenyl-3-yl)-5-hydroxy-6-oxo-1,6-dihydropyridine-2-carbonitrile;
5-Biphenyl-3-yl-4-fluoro-3-hydroxypyridin-2(1H)-one;
5-Biphenyl-3-yl-4-fluoro-3-hydroxy-1-methylpyridin-2(1H)-one;
5-(Biphenyl-3-yl)-3-hydroxy-6-(1-hydroxy-2-phenylethyl)-1-methylpyridin-2(1H)-one;
6-(1-Benzyl-1H-pyrazol-4-yl)-3-hydroxy-1H-pyridin-2-one;
6-(4-Chlorophenyl)-3-hydroxy-1-methylpyridin-2(1H)-one;
including tautomers or pharmaceutically acceptable salts and individual enantiomers and diastereomers thereof.

11. A pharmaceutical composition comprising an inert carrier and an effective amount of a compound according to claim 1.

12. The composition according to claim 11 further comprising one or more therapeutically active compounds selected from the group consisting of opiate agonists or antagonists, calcium channel antagonists, 5HT, 5-HT$_{1A}$ complete or partial receptor agonists or antagonists, sodium channel antagonists, N-methyl-D-aspartate (NMDA) receptor agonists or antagonists, COX-2 selective inhibitors, neurokinin receptor 1 (NK1) antagonists, non-steroidal anti-inflammatory drugs (NSAID), selective serotonin reuptake inhibitors (SSRI) and/or selective serotonin and norepinephrine reuptake inhibitors (SSNRI), tricyclic antidepressant drugs, norepinephrine modulators, lithium, valproate, norepinephrine reuptake inhibitors, monoamine oxidase inhibitors (MAOIs), reversible inhibitors of monoamine oxidase (RIMAs), alpha-adrenoreceptor antagonists, atypical antidepressants, benzodiazepines, corticotropin releasing factor (CRF) antagonists, neurontin (gabapentin) and pregabalin.

13. A compound of structural formula I:

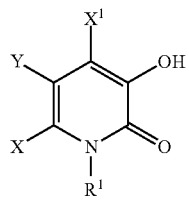

including tautomers or pharmaceutically acceptable salts and individual enantiomers and diastereomers thereof wherein:

Y represents CN, $C_{2-6}$ alkynyl, $CH_2C_{5-10}$ heterocyclyl, $(CH_2)_2C_{5-10}$ heterocyclyl, $(CH_2)_3C_{5-10}$ heterocyclyl, $(CH_2)_4C_{5-10}$ heterocyclyl, $(CH_2)_5 C_{5-10}$ heterocyclyl, $(CH_2)_nC_{6-10}$ aryl, said alkynyl, heterocyclyl and aryl substituted with 1 to 3 groups of $R^a$;

X represents hydrogen, halo, CN, $C_{1-6}$ alkyl, $C_{2-6}$ alkynyl, $(CH_2)_nC_{5-10}$ heterocyclyl, said alkyl and heterocyclyl optionally substituted with 1 to 3 groups of $R^a$;

$X^1$ represents hydrogen, halo, CN, $C_{1-6}$ alkyl, $C_{2-6}$ alkynyl, $(CH_2)_nC_{6-10}$ aryl, $(CH_2)_nC_{5-10}$ heterocyclyl, said alkyl, heterocyclyl, and aryl optionally substituted with 1 to 3 groups of $R^a$;

$R^1$ represent halo, CN, $C_{2-6}$ alkynyl, $(CH_2)_nC_{6-10}$ aryl, $(CH_2)_nC_{5-10}$ heterocyclyl, said alkynyl, heterocyclyl, and aryl optionally substituted with 1 to 3 groups of $R^a$;

$R^2$ represents H, OH, $C_{1-6}$ alkyl, $N(CH_3)_2$, $(CH_2)_nC_{3-10}$ cycloalkyl, $(CH_2)_nC_{5-10}$ heterocyclyl, $(CH_2)_nC_{6-10}$ aryl, said aryl and heterocyclyl optionally substituted with 1 to 3 groups of $R^a$;

$R^a$ represents $C_{1-6}$ alkyl, halogen, hydroxyl, $C_{2-4}$alkynyl, $(CH_2)_nCF_3$, $OCHF_2$, $OCF_3$, $C_{3-6}$ cycloalkyl, $NR^2C(O)R^2$, $C(O)N(R^2)_2$, $C(R^2)_2OR^2$, $C(O)R^2$, $NO_2$, CN, $N(R^2)_2$, $(CH_2)_nC(O)OR^2$, $SO_2R^2$, $NHSO_2R^2$, $OR^2$, $(CH_2)_nC_{5-10}$ heterocyclyl, $C(O)(CH_2)_nC_{5-10}$ heterocyclyl, $(CH_2)_nC_{6-10}$ aryl, or $C(O)(CH_2)_nC_{6-10}$ aryl, said alkyl, alkynyl, cycloalkyl, heterocyclyl and aryl optionally substituted with 1 to 3 groups of $R^b$;

$R^b$ represents $C_{1-6}$ alkyl, halogen, $CHF_2$, $OCHF_2$, —O—, $N(R^2)_2$, $CH_2OH$, $(CH_2)_nC_{6-10}$ aryl, $(CH_2)_nC_{5-10}$ heterocyclyl, $OR^2$, $C_{3-6}$cycloalkyl, $(CH_2)_nCF_3$, or CN; and n represents 0 to 5.

14. A compound of structural formula I:

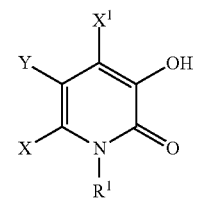

including tautomers or pharmaceutically acceptable salts and individual enantiomers and diastereomers thereof wherein:

Y represents $C_{2-6}$ alkynyl, $CH_2C_{5-10}$ heterocyclyl, $(CH_2)_2C_{5-10}$ heterocyclyl, $(CH_2)_3C_{5-10}$ heterocyclyl, $(CH_2)_4C_{5-10}$ heterocyclyl, $(CH_2)_5 C_{5-10}$ heterocyclyl, $CH_2C_{6-10}$ aryl, $(CH_2)_2C_{6-10}$ aryl, $(CH_2)_3C_{6-10}$ aryl, $(CH_2)_4C_{6-10}$ aryl, $(CH_2)_5C_{6-10}$ aryl, said alkynyl, heterocyclyl and aryl substituted with 1 to 3 groups of $R^a$;

X, $X^1$, and $R^1$ independently represent hydrogen, halo, CN, $C_{1-6}$ alkyl, $C_{2-6}$ alkynyl, $(CH_2)_nC_{6-10}$ aryl, $(CH_2)_nC_{5-10}$ heterocyclyl, said alkyl, heterocyclyl, and aryl optionally substituted with 1 to 3 groups of $R^a$;

$R^2$ represents H, OH, $C_{1-6}$ alkyl, $N(CH_3)_2$, $(CH_2)_nC_{3-10}$ cycloalkyl, $(CH_2)_nC_{5-10}$ heterocyclyl, $(CH_2)_nC_{6-10}$ aryl, said aryl and heterocyclyl optionally substituted with 1 to 3 groups of $R^a$;

$R^a$ represents $C_{1-6}$ alkyl, halogen, hydroxyl, $C_{2-4}$alkynyl, $(CH_2)_nCF_3$, $OCHF_2$, $OCF_3$, $C_{3-6}$ cycloalkyl, $NR^2C(O)R^2$, $C(O)N(R^2)_2$, $C(R^2)_{2OR}^2$, $C(O)R^2$, $NO_2$, CN, $N(R^2)_2$, $(CH_2)_nC(O)OR^2$, $SO_2R^2$, $NHSO_2R^2$, $OR^2$, $(CH_2)_nC_{5-10}$ heterocyclyl, $C(O)(CH_2)_nC_{5-10}$ heterocyclyl, $(CH_2)_nC_{6-10}$ aryl, or $C(O)(CH_2)_nC_{6-10}$ aryl, said alkyl, alkynyl, cycloalkyl, heterocyclyl and aryl optionally substituted with 1 to 3 groups of $R^b$;

$R^b$ represents $C_{1-6}$ alkyl, halogen, $CHF_2$, $OCHF_2$, —O—, $N(R^2)_2$, $CH_2OH$, $(CH_2)_nC_{6-10}$ aryl, $(CH_2)_nC_{5-10}$ heterocyclyl, $OR^2$, $C_{3-6}$cycloalkyl, $(CH_2)_nCF_3$, or CN; and n represents 0 to 5.

15. A compound of structural formula I:

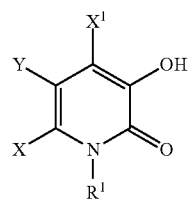

including tautomers or pharmaceutically acceptable salts and individual enantiomers and diastereomers thereof wherein:

Y represents $C_{2-6}$ alkynyl, $(CH_2)_nC_{5-10}$ heterocyclyl, $(CH_2)_nC_{6-10}$ aryl, said alkynyl, heterocyclyl and aryl optionally substituted with 1 to 3 groups of $R^a$; provided that when Y is $(CH_2)_nC_{5-10}$ heterocyclyl, Y is quinolinyl, isoquinolinyl, thiazolyl, triazolyl, pyrrolyl, pyrrolidinyl, pyrazolyl or imidazolyl;

X, $X^1$, and $R^1$ independently represent hydrogen, halo, CN, $C_{1-6}$ alkyl, $C_{2-6}$ alkynyl, $(CH_2)_nC_{6-10}$ aryl, $(CH_2)_nC_{5-10}$ heterocyclyl, said alkyl, heterocyclyl, and aryl optionally substituted with 1 to 3 groups of $R^a$; provided that when Y is $(CH_2)_nC_{6-10}$ aryl, X and $X^1$ both are hydrogen;

$R^2$ represents H, OH, $C_{1-6}$ alkyl, $N(CH_3)_2$, $(CH_2)_nC_{3-10}$ cycloalkyl, $(CH_2)_nC_{5-10}$ heterocyclyl, $(CH_2)_nC_{6-10}$ aryl, said aryl and heterocyclyl optionally substituted with 1 to 3 groups of $R^a$;

$R^a$ represents $C_{1-6}$ alkyl, halogen, hydroxyl, $C_{2-4}$alkynyl, $(CH_2)_nCF_3$, $OCHF_2$, $OCF_3$, $C_{3-6}$ cycloalkyl, $NR^2C(O)R^2$, $C(O)N(R^2)_2$, $C(R^2)_2OR^2$, $C(O)R^2$, $NO_2$, CN, $N(R^2)_2$, $(CH_2)_nC(O)OR^2$, $SO_2R^2$, $NHSO_2R^2$, $OR^2$, $(CH_2)_nC_{5-10}$ heterocyclyl, $C(O)(CH_2)_nC_{5-10}$ heterocyclyl, $(CH_2)_nC_{6-10}$ aryl, or $C(O)(CH_2)_nC_{6-10}$ aryl, said alkyl, alkynyl, cycloalkyl, heterocyclyl and aryl optionally substituted with 1 to 3 groups of $R^b$;

$R^b$ represents $C_{1-6}$ alkyl, halogen, $CHF_2$, $OCHF_2$, —O—, $N(R^2)_2$, $CH_2OH$, $(CH_2)_nC_{6-10}$ aryl, $(CH_2)_nC_{5-10}$ heterocyclyl, $OR^2$, $C_{3-6}$cycloalkyl, $(CH_2)_nCF_3$, or CN; and n represents 0 to 5.

16. A method of augmentation of effect of anti-psychotics in the treatment of schizophrenia, or treating major depressive disorder, anxiety disorder, obsessive-compulsive disorder, bipolar disorder, ADHD, substance dependency, the weight gain or food cravings associated with quitting smoking or the use of antipsychotics, or Parkinson's disease, comprising administering to said patient a therapeutically effective amount of a compound according to formula I in claim 1 or pharmaceutically acceptable salts, and individual enantiomers and diastereomers thereof.

\* \* \* \* \*